United States Patent
Kole et al.

(10) Patent No.: US 10,106,796 B2
(45) Date of Patent: Oct. 23, 2018

(54) COMPOUND AND METHOD FOR TREATING MYOTONIC DYSTROPHY

(71) Applicant: Sarepta Therapeutics, Inc., Corvallis, OR (US)

(72) Inventors: Ryszard Kole, Corvallis, OR (US); Gunnar J. Hanson, Bothell, WA (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/464,561

(22) Filed: Aug. 20, 2014

(65) Prior Publication Data

US 2015/0141321 A1    May 21, 2015

Related U.S. Application Data

(63) Continuation of application No. 14/038,314, filed on Sep. 26, 2013, now Pat. No. 8,835,402, which is a continuation of application No. 13/101,942, filed on May 5, 2011, which is a continuation-in-part of application No. 12/493,140, filed on Jun. 26, 2009.

(51) Int. Cl.
| C12N 15/113 | (2010.01) |
| C12N 15/87  | (2006.01) |

(52) U.S. Cl.
CPC ........ *C12N 15/1137* (2013.01); *C12N 15/113* (2013.01); *C12N 15/87* (2013.01); *C07K 2319/33* (2013.01); *C12N 2310/113* (2013.01); *C12N 2310/3233* (2013.01); *C12N 2810/40* (2013.01)

(58) Field of Classification Search
None
See application file for complete search history.

(56) References Cited

U.S. PATENT DOCUMENTS

| 5,525,465 A | 6/1996 | Haralambidis et al. |
| 5,747,641 A | 5/1998 | Frankel et al. |
| 5,849,727 A | 12/1998 | Porter et al. |
| 6,159,946 A | 12/2000 | Zalewski et al. |
| 6,303,573 B1 | 10/2001 | Ruoslahti et al. |
| 6,365,351 B1 | 4/2002 | Iversen |
| 6,495,663 B1 | 12/2002 | Rothbard et al. |
| 6,645,974 B2 | 11/2003 | Hutchinson et al. |
| 6,669,951 B2 | 12/2003 | Rothbard et al. |
| 7,468,418 B2 * | 12/2008 | Iversen ............ A61K 47/48246 530/300 |
| 2003/0032593 A1 | 2/2003 | Wender et al. |
| 2003/0040466 A1 | 2/2003 | Vodyanoy et al. |
| 2003/0045488 A1 | 3/2003 | Brown et al. |
| 2003/0087861 A1 | 5/2003 | Iversen |
| 2003/0185788 A1 | 10/2003 | Rothbard et al. |
| 2003/0235845 A1 | 12/2003 | Van Ommen et al. |
| 2004/0170955 A1 | 9/2004 | Arap et al. |
| 2005/0171026 A1 | 8/2005 | Hagiwara et al. |
| 2006/0014712 A1 | 1/2006 | Neuman |
| 2006/0078542 A1 | 4/2006 | Mah et al. |
| 2006/0269911 A1 | 11/2006 | Iversen et al. |
| 2006/0276425 A1 | 12/2006 | Mourich et al. |
| 2007/0135333 A1 | 6/2007 | Geller et al. |
| 2009/0099066 A1 | 4/2009 | Moulton et al. |
| 2010/0184833 A1 | 7/2010 | De Kimpe et al. |
| 2010/0190689 A1 | 7/2010 | Thornton et al. |
| 2011/0118334 A1* | 5/2011 | Iversen ............ C12N 15/1131 514/44 A |
| 2012/0148622 A1 | 6/2012 | tenOever |

FOREIGN PATENT DOCUMENTS

| WO | 00/44897 A1 | 8/2000 |
| WO | 00/71706 A1 | 11/2000 |
| WO | 01/62297 A1 | 8/2001 |
| WO | 03/068942 A2 | 8/2003 |
| WO | 2005115479 A2 | 12/2005 |
| WO | 2006047683 A2 | 5/2006 |
| WO | 2006086667 A2 | 8/2006 |
| WO | 2007030576 A2 | 3/2007 |
| WO | 2007/056466 A2 | 5/2007 |
| WO | 2008008113 A1 | 1/2008 |
| WO | 2008036127 A2 | 3/2008 |
| WO | 2009/005793 A3 | 1/2009 |

OTHER PUBLICATIONS

Abes et al., "Arginine-rich cell penetrating peptides: design, structure-activity, and applications to alter pre-mRNA splicing by steric-block oligonucleotides," *Journal of Peptide Science* 14:455-460, 2008.

Abes et al., "Vectorization of morpholino oligomers by the (R-Ahx-R)4 peptide allows efficient splicing correction in the absence of endosomolytic agents," *Journal of Controlled Release* 116(3):304-313, 2006.

Alter et al., "Systemic delivery of morpholino oligonucleotide restores dystrophin expression bodywide and improves dystophic pathology," *Nature Medicine* 12(2):175-177, 2006.

Arora et al., "Bioactivity and efficacy of antisense morpholino oligomers targeted to c-myc and Cytochrome P-450 3A2 following oral administration in rats," *Journal of Pharmaceutical Science* 91(4):1009-1018, 2002.

Burrer et al., "Antiviral effects of antisense morpholino oligomers in murine coronavirus infection models," *Journal of Virology* 81(11):5634-5648, 2007.

Chen et al., "A concise method for the preparation of peptide and Arginine-rich peptide-conjugated antisense oligonucleotide," *Bioconjugate Chemistry* 14:532-538, 2003.

Dapic et al., "Biophysical and biological properties of quadruplex oligodeoxyribonucleotides," *Nucleic Acids Research* 31(8):2097-2107, 2003.

(Continued)

*Primary Examiner* — Tracy Vivlemore
(74) *Attorney, Agent, or Firm* — Brian C. Trinque; Alan W. Steele; Lathrop Gage LLP

(57) ABSTRACT

Provided are 9-base morpholino antisense compounds targeted to polyCUG repeats in the 3'UTR region of dystrophia myotonica protein kinase (DMPK) mRNA, and related methods for treating myotonic dystrophy DM1.

16 Claims, 3 Drawing Sheets

Specification includes a Sequence Listing.

(56) References Cited

OTHER PUBLICATIONS

Devi, "Prostate cancer: status of current treatments and emerging antisense-based therapies," *Current Opinion Therapies* 4(2):138-148, 2002.
EMBL/Genbank/DDBJ database (Deshazer), Sequence CH899747, Retrieved from URL=http://www.ebi.ac.uk/sgi-bin/emblfetch?style+html&id+CH899747, 196 pages, May 26, 2007.
Eriksson et al., "Cell permeabilization and uptake of antisense peptide-peptide nucleic acid (PNA) into *Escherichia coli,*" *Journal of Biological Chemistry* 277(9):7144-7147, 2002.
Gebski et al., "Morpholino antisense oligonucleotide induced dystrophin exon 23 skipping in mdx mouse muscle," *Human Molecular Genetics* 12(15):1801-1811, 2003.
Ghosh et al., "Intracellular delivery strategies for antisense Phosphorodiamidate morpholino oligomers," *Antisense & Nucleic Acid Drug Development* 10:263-274, 2000.
Hudziak et al., "Resistance of morpholino Phosphorodiamidate oligomers to enzymatic degradation," *Antisense Nucleic Acid Drug Dev.* 6:267-272, 1996.
International Preliminary Report on Patentability for corresponding International Application No. PCT/US08/08168, dated Jun. 30, 2008, 10 pages.
International Search Report and Written Opinion for corresponding International Application No. PCT/US2008/008168, dated Mar. 19, 2009, 13 pages.
International Search Report for corresponding International Application No. PCT/US2004/013660, dated Feb. 21, 2005, 5 pages.
Iversen, "Phosphorodiamidate morpholino oligomers: favorable properties for sequence-specific gene inactivation," *Current Opinion in molecular Therapeutics* 3(3):235-238, 2001.
Jearawiriyapaisarn et al., "Sustained Dystrophin Expression Induced by Peptide-conjugated Morpholino Oligomers in the Muscles of mdx Mice," *Mol. Therapy* 16(9):1624-1629, 2008.
Kang et al., "Up-regulation of luciferase gene expression with antisense oligonucleotides: implications and applications in functional assay development," *Biochemistry* 37(18):6235-6239, 1998.
Knapp et al., "resistance to chemotherapeutic drugs overcome by c-Myc inhibition in a Lewis lung carcinoma murine model," *Anticancer Drugs* 14(1):39-47, 2003.
Kolonin et al., "Synchronous selection of homing peptides for multiple tissues by in vivo phage display," *The FASEB Journal* 20(7):979-981, 2006.
Lebleu et al., "Cell penetrating peptide conjugate of steric block oligonucleotides," *Advanced Drug Delivery Reviews* 60:517-529, 2008.
Marshall et al., "Arginine-rich cell-penetrating peptides facilitate delivery of antisense oligomers into murine leukocytes and alter pre-mRNA splicing," *Journal of Immunological Methods* 325:114-126, 2007.
Meade et al., "Exogenous siRNA delivery using peptide transduction domains/cell penetrating peptides," *Advance Drug Delivery Reviews* 59(2-3):134-140, 2007.
Mizutani et al "Enhancement of sensitivity of urinary bladder tumor cells to cisplatin by c-myc antisense oligonucleotide," *Cancer* 74(9):2546-2554, 1994.
Moulton et al., "Cellular uptake of antisense morpholino oligomers conjugated to Arginine-rich peptides," *Bioconjugate Chemistry* 15:290-299, 2004.
Moulton et al., "HIV Tat peptide enhances cellular delivery of antisense morpholino oligomers," *Antisense and Nucleic Acid Drug Development* 13(1):31-43, 2003.
Richard et al., "Cell-penetrating peptides. A reevaluation of the mechanism of cellular uptake," *Journal of Biological Chemistry* 278(1):585-590, 2003.
Rothbard et al., "Arginine-rich molecular transporters for drug delivery: role of backbone spacing in cellular uptake," *J. Med. Chem.* 45(17):3612-3618, 2002.
Samoylova et al., "Elucidation of muscle-binding peptides by phage display screening," *Muscle & Nerve* 22(4):460-466, 1999.
Shafer et al., "Biological aspects of DNA/RNA quadruplexes," *Biopolymers* 56(3):209-227, 2000.
Stein et al., "Inhibition of Versivirus infections in mammalian tissue culture with antisense morpholino oligomers," *Antisense Nucleic Acid Drug Dev.* 11(5):317-325, 2001.
Summerton et al. "Morpholino Antisense Oligomers: Design, Preparation, and Properties," *Antisense Nucleic Acid Drug Dev.* 7:187-195, 1997.
Vanin et al., "Synthesis and application of cleavable photoactivable heterobifunctional reagents," *Biochemistry* 20(24):6754-6760, 1981.
Wender et al., "Oligocarbamate molecule transporters: design, synthesis, and biological evaluation of a new class of transporters for drug delivery," *J. Am. Chem. Soc.* 124:13382-13383, 2002.
Wender et al., "The design, synthesis, and evaluation of molecules that enable or enhance cellular uptake: peptoid molecular transporters," *Proc. Natl. Acad. Sci. USA* 97(24):13003-13008, 2000.
Wu et al., "Cell-penetrating peptides as transporters for morpholino oligomers: effects of amino acid composition on intracellular delivery and cytotoxicity," *Nulceic Acids Res.* 35(15):5182-5191, 2007.
Youngblood et al., "Stability of cell-penetrating peptide-morpholino oligomers conjugates in human serum and in cells," *Bioconjugate Chemistry* 18(1):50-60, 2007.
Zubin et al., "Oligonucleotide-peptide conjugates as potential antisense agents," *FEBS Letters* 456(1):59-62, 1999.

\* cited by examiner

SEQUENCE LISTING

```
<160> NUMBER OF SEQ ID NOS: 62

<210> SEQ ID NO 1
<211> LENGTH: 9
<212> TYPE: DNA
<213> ORGANISM: Artificial Sequence
<220> FEATURE:
<223> OTHER INFORMATION: Antisense oligomer

<400> SEQUENCE: 1 cagcagcag                                                                9

<210> SEQ ID NO 2
<211> LENGTH: 12
<212> TYPE: DNA
<213> ORGANISM: Artificial Sequence
<220> FEATURE:
<223> OTHER INFORMATION: Antisense oligomer

<400> SEQUENCE: 2
cagcagcagc ag                                                           12

<210> SEQ ID NO 3
<211> LENGTH: 15
<212> TYPE: DNA
<213> ORGANISM: Artificial Sequence
<220> FEATURE:
<223> OTHER INFORMATION: Antisense oligomer

<400> SEQUENCE: 3
cagcagcagc agcag                                                        15

<210> SEQ ID NO 4
<211> LENGTH: 18
<212> TYPE: DNA
<213> ORGANISM: Artificial Sequence
<220> FEATURE:
<223> OTHER INFORMATION: Antisense oligomer

<400> SEQUENCE: 4
```

```
cagcagcagc agcagcag                                                 18

<210> SEQ ID NO 5
<211> LENGTH: 9
<212> TYPE: DNA
<213> ORGANISM: Artificial Sequence
<220> FEATURE:
<223> OTHER INFORMATION: Antisense oligomer

<400> SEQUENCE: 5 agcagcagc                                                            9

<210> SEQ ID NO 6
<211> LENGTH: 12
<212> TYPE: DNA
<213> ORGANISM: Artificial Sequence
<220> FEATURE:
<223> OTHER INFORMATION: Antisense oligomer

<400> SEQUENCE: 6
agcagcagca gc                                                       12

<210> SEQ ID NO 7
<211> LENGTH: 15
<212> TYPE: DNA
<213> ORGANISM: Artificial Sequence
<220> FEATURE:
<223> OTHER INFORMATION: Antisense oligomer

<400> SEQUENCE: 7
agcagcagca gcagc                                                    15

<210> SEQ ID NO 8
<211> LENGTH: 18
<212> TYPE: DNA
<213> ORGANISM: Artificial Sequence
<220> FEATURE:
<223> OTHER INFORMATION: Antisense oligomer

<400> SEQUENCE: 8
agcagcagca gcagcagc                                                 18

<210> SEQ ID NO 9
<211> LENGTH: 9
<212> TYPE: DNA
<213> ORGANISM: Artificial Sequence
<220> FEATURE:
<223> OTHER INFORMATION: Antisense oligomer

<400> SEQUENCE: 9 gcagcagca                                                            9

<210> SEQ ID NO 10
<211> LENGTH: 12
<212> TYPE: DNA
<213> ORGANISM: Artificial Sequence
<220> FEATURE:
<223> OTHER INFORMATION: Antisense oligomer

<400> SEQUENCE: 10
gcagcagcag ca                                                       12

<210> SEQ ID NO 11
<211> LENGTH: 15
<212> TYPE: DNA
```

```
<213> ORGANISM: Artificial Sequence
<220> FEATURE:
<223> OTHER INFORMATION: Antisense oligomer

<400> SEQUENCE: 11
gcagcagcag cagca                                                          15

<210> SEQ ID NO 12
<211> LENGTH: 18
<212> TYPE: DNA
<213> ORGANISM: Artificial Sequence
<220> FEATURE:
<223> OTHER INFORMATION: Antisense oligomer

<400> SEQUENCE: 12
gcagcagcag cagcagca                                                       18

<210> SEQ ID NO 13
<211> LENGTH: 25
<212> TYPE: DNA
<213> ORGANISM: Artificial Sequence
<220> FEATURE:
<223> OTHER INFORMATION: Antisense oligomer

<400> SEQUENCE: 13
agcagcagca gcagcagcag cagca                                               25

<210> SEQ ID NO 14
<211> LENGTH: 25
<212> TYPE: DNA
<213> ORGANISM: Artificial Sequence
<220> FEATURE:
<223> OTHER INFORMATION: Antisense oligomer

<400> SEQUENCE: 14
cagcagcagc agcagcagca gcagc                                               25

<210> SEQ ID NO 15
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (1)...(2)
<223> OTHER INFORMATION: cationic linkage, such as 1-piperazinyl
<220> FEATURE:
<221> NAME/KEY: misc_feature
<222> LOCATION: (4)...(5)
<223> OTHER INFORMATION: cationic linkage, such as 1-piperazinyl
<220> FEATURE:
<221> NAME/KEY: misc_feature
<222> LOCATION: (7)...(8)
<223> OTHER INFORMATION: cationic linkage, such as 1-piperazinyl

<400> SEQUENCE: 15 cagcagcag                                                                  9

<210> SEQ ID NO 16
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (1)...(2)
<223> OTHER INFORMATION: cationic linkage, such as 1-piperazinyl
```

```
<400> SEQUENCE: 16 cagcagcag                                                                9

<210> SEQ ID NO 17
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (7)...(8)
<223> OTHER INFORMATION: cationic linkage, such as 1-piperazinyl

<400> SEQUENCE: 17 cagcagcag                                                                9

<210> SEQ ID NO 18
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (4)...(5)
<223> OTHER INFORMATION: cationic linkage, such as 1-piperazinyl

<400> SEQUENCE: 18 cagcagcag                                                                9

<210> SEQ ID NO 19
<211> LENGTH: 9
<212> TYPE: DNA
<213> ORGANISM: Artificial Sequence
<220> FEATURE:
<223> OTHER INFORMATION: Antisense oligomer

<400> SEQUENCE: 19 caggcaggc                                                                9

<210> SEQ ID NO 20
<211> LENGTH: 12
<212> TYPE: DNA
<213> ORGANISM: Artificial Sequence
<220> FEATURE:
<223> OTHER INFORMATION: Antisense oligomer

<400> SEQUENCE: 20
caggcaggca gg                                                           12

<210> SEQ ID NO 21
<211> LENGTH: 9
<212> TYPE: DNA
<213> ORGANISM: Artificial Sequence
<220> FEATURE:
<223> OTHER INFORMATION: Antisense oligomer

<400> SEQUENCE: 21 aggcaggca                                                                9

<210> SEQ ID NO 22
<211> LENGTH: 12
<212> TYPE: DNA
<213> ORGANISM: Artificial Sequence
<220> FEATURE:
```

```
<223> OTHER INFORMATION: Antisense oligomer

<400> SEQUENCE: 22
aggcaggcag gc                                                              12

<210> SEQ ID NO 23
<211> LENGTH: 9
<212> TYPE: DNA
<213> ORGANISM: Artificial Sequence
<220> FEATURE:
<223> OTHER INFORMATION: Antisense oligomer

<400> SEQUENCE: 23 ggcaggcag                                                                   9

<210> SEQ ID NO 24
<211> LENGTH: 12
<212> TYPE: DNA
<213> ORGANISM: Artificial Sequence
<220> FEATURE:
<223> OTHER INFORMATION: Antisense oligomer

<400> SEQUENCE: 24
ggcaggcagg ca                                                              12

<210> SEQ ID NO 25
<211> LENGTH: 24
<212> TYPE: DNA
<213> ORGANISM: Artificial Sequence
<220> FEATURE:
<223> OTHER INFORMATION: Antisense oligomer

<400> SEQUENCE: 25
caggcaggca ggcaggcagg cagg                                                 24

<210> SEQ ID NO 26
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (1)...(2)
<223> OTHER INFORMATION: cationic linkage, such as 1-piperazinyl
<220> FEATURE:
<221> NAME/KEY: misc_feature
<222> LOCATION: (5)...(6)
<223> OTHER INFORMATION: cationic linkage, such as 1-piperazinyl

<400> SEQUENCE: 26 caggcaggc                                                                   9

<210> SEQ ID NO 27
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (1)...(2)
<223> OTHER INFORMATION: cationic linkage, such as 1-piperazinyl
<220> FEATURE:
<221> NAME/KEY: misc_feature
<222> LOCATION: (5)...(6)
<223> OTHER INFORMATION: cationic linkage, such as 1-piperazinyl

<400> SEQUENCE: 27
```

```
caggcaggc                                                            9

<210> SEQ ID NO 28
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (1)...(2)
<223> OTHER INFORMATION: cationic linkage, such as 1-piperazinyl

<400> SEQUENCE: 28 caggcaggc                                                            9

<210> SEQ ID NO 29
<211> LENGTH: 9
<212> TYPE: DNA
<213> ORGANISM: Artificial Sequence
<220> FEATURE:
<223> OTHER INFORMATION: Antisense oligomer
<220> FEATURE:
<221> NAME/KEY: misc_feature
<222> LOCATION: (5)...(6)
<223> OTHER INFORMATION: cationic linkage, such as 1-piperazinyl

<400> SEQUENCE: 29 caggcaggc                                                            9

<210> SEQ ID NO 30
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 30

Arg Arg Arg Gln Arg Arg Lys Lys Arg
 1               5

<210> SEQ ID NO 31
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 31

Arg Lys Lys Arg Arg Gln Arg Arg Arg
 1               5

<210> SEQ ID NO 32
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 32

Arg Arg Arg Arg Arg Arg Arg Arg Arg Phe Phe
 1               5                  10

<210> SEQ ID NO 33
<211> LENGTH: 11
<212> TYPE: PRT
<213> ORGANISM: Artificial Sequence
```

```
<220> FEATURE:
<223> OTHER INFORMATION: Cell penetrating peptide

<400> SEQUENCE: 33

Arg Arg Arg Arg Arg Phe Phe Arg Arg Arg
 1               5                  10

<210> SEQ ID NO 34
<211> LENGTH: 4
<212> TYPE: PRT
<213> ORGANISM: Artificial Sequence
<220> FEATURE:
<223> OTHER INFORMATION: Cell penetrating peptide

<400> SEQUENCE: 34

Arg Arg Arg Arg
 1

<210> SEQ ID NO 35
<211> LENGTH: 5
<212> TYPE: PRT
<213> ORGANISM: Artificial Sequence
<220> FEATURE:
<223> OTHER INFORMATION: Cell penetrating peptide

<400> SEQUENCE: 35

Arg Arg Arg Arg Arg
 1               5

<210> SEQ ID NO 36
<211> LENGTH: 6
<212> TYPE: PRT
<213> ORGANISM: Artificial Sequence
<220> FEATURE:
<223> OTHER INFORMATION: Cell penetrating peptide

<400> SEQUENCE: 36

Arg Arg Arg Arg Arg Arg
 1               5

<210> SEQ ID NO 37
<211> LENGTH: 7
<212> TYPE: PRT
<213> ORGANISM: Artificial Sequence
<220> FEATURE:
<223> OTHER INFORMATION: Cell penetrating peptide

<400> SEQUENCE: 37

Arg Arg Arg Arg Arg Arg Arg
 1               5

<210> SEQ ID NO 38
<211> LENGTH: 8
<212> TYPE: PRT
<213> ORGANISM: Artificial Sequence
<220> FEATURE:
<223> OTHER INFORMATION: Cell penetrating peptide

<400> SEQUENCE: 38

Arg Arg Arg Arg Arg Arg Arg Arg
 1               5

<210> SEQ ID NO 39
<211> LENGTH: 9
<212> TYPE: PRT
<213> ORGANISM: Artificial Sequence
<220> FEATURE:
```

```
<223> OTHER INFORMATION: Cell penetrating peptide

<400> SEQUENCE: 39

Arg Arg Arg Arg Arg Arg Arg Arg Arg
 1               5

<210> SEQ ID NO 40
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11
<223> OTHER INFORMATION: Acp

<400> SEQUENCE: 40

Arg Xaa Arg Arg Xaa Arg Arg Xaa Arg Arg Xaa Arg
 1               5                  10

<210> SEQ ID NO 41
<211> LENGTH: 15
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11, 14
<223> OTHER INFORMATION: Acp

<400> SEQUENCE: 41

Arg Xaa Arg Arg Xaa Arg Arg Xaa Arg Arg Xaa Arg Arg Xaa Arg
 1               5                  10                  15

<210> SEQ ID NO 42
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 8
<223> OTHER INFORMATION: Acp
<220> FEATURE:
<221> NAME/KEY: MOD_RES
<222> LOCATION: 5, 11
<223> OTHER INFORMATION: bAla

<400> SEQUENCE: 42

Arg Xaa Arg Arg Ala Arg Arg Xaa Arg Arg Ala Arg
 1               5                  10

<210> SEQ ID NO 43
<211> LENGTH: 15
<212> TYPE: PRT
<213> ORGANISM: Artificial Sequence
<220> FEATURE:
<223> OTHER INFORMATION: Cell penetrating peptide

<400> SEQUENCE: 43

Arg Ala Arg Arg Ala Arg Arg Ala Arg Arg Ala Arg Phe Phe Cys
 1               5                  10                  15

<210> SEQ ID NO 44
<211> LENGTH: 15
<212> TYPE: PRT
```

```
<213> ORGANISM: Artificial Sequence
<220> FEATURE:
<223> OTHER INFORMATION: Cell penetrating peptide

<400> SEQUENCE: 44

Arg Gly Arg Arg Gly Arg Arg Gly Arg Arg Gly Arg Phe Phe Cys
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: Muscle-specific Homing Peptide

<400> SEQUENCE: 45

Ala Ser Ser Leu Asn Ile Ala
1               5

<210> SEQ ID NO 46
<211> LENGTH: 6
<212> TYPE: PRT
<213> ORGANISM: Artificial Sequence
<220> FEATURE:
<223> OTHER INFORMATION: Muscle-specific Homing Peptide

<400> SEQUENCE: 46

Ser Leu Gly Ser Phe Pro
1               5

<210> SEQ ID NO 47
<211> LENGTH: 6
<212> TYPE: PRT
<213> ORGANISM: Artificial Sequence
<220> FEATURE:
<223> OTHER INFORMATION: Muscle-specific Homing Peptide

<400> SEQUENCE: 47

Ser Gly Ala Ser Ala Val
1               5

<210> SEQ ID NO 48
<211> LENGTH: 6
<212> TYPE: PRT
<213> ORGANISM: Artificial Sequence
<220> FEATURE:
<223> OTHER INFORMATION: Muscle-specific Homing Peptide

<400> SEQUENCE: 48

Gly Arg Ser Gly Ala Arg
1               5

<210> SEQ ID NO 49
<211> LENGTH: 12
<212> TYPE: PRT
<213> ORGANISM: Artificial Sequence
<220> FEATURE:
<223> OTHER INFORMATION: Muscle-specific Homing Peptide

<400> SEQUENCE: 49

Thr Ala Arg Gly Glu His Lys Glu Glu Glu Leu Ile
1               5                   10

<210> SEQ ID NO 50
<211> LENGTH: 20
<212> TYPE: PRT
<213> ORGANISM: Artificial Sequence
```

```
<220> FEATURE:
<223> OTHER INFORMATION: Muscle-specific Homing Peptide

<400> SEQUENCE: 50

Trp Leu Ser Glu Ala Gly Pro Val Val Thr Val Arg Ala Leu Arg Gly
1               5                   10                  15

Thr Gly Ser Trp
            20

<210> SEQ ID NO 51
<211> LENGTH: 11
<212> TYPE: PRT
<213> ORGANISM: Artificial Sequence
<220> FEATURE:
<223> OTHER INFORMATION: Muscle-specific Homing Peptide

<400> SEQUENCE: 51

Val Thr Val Arg Ala Leu Arg Gly Thr Ser Trp
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Muscle-specific Homing Peptide

<400> SEQUENCE: 52

Val Val Thr Val Arg Ala Leu Arg Gly Thr Gly Ser Trp
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Muscle-specific Homing Peptide

<400> SEQUENCE: 53

Cys Arg Pro Pro Arg
1               5

<210> SEQ ID NO 54
<211> LENGTH: 12
<212> TYPE: PRT
<213> ORGANISM: Artificial Sequence
<220> FEATURE:
<223> OTHER INFORMATION: Muscle-specific Homing Peptide

<400> SEQUENCE: 54

Ser Lys Thr Phe Asn Thr His Pro Gln Ser Thr Pro
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 8, 13
<223> OTHER INFORMATION: Xaa = 5-aminopentanoic acid or 6-aminohexanoic
      acid or 7-aminoheptanoic acid
<220> FEATURE:
<221> NAME/KEY: MOD_RES
<222> LOCATION: 5, 11
<223> OTHER INFORMATION: Xaa = 5-aminopentanoic acid or 6-aminohexanoic
```

```
                acid or 7-aminoheptanoic acid or beta-alanine
<220> FEATURE:
<221> NAME/KEY: MOD_RES
<222> LOCATION: 14
<223> OTHER INFORMATION: bAla

<400> SEQUENCE: 55

Arg Xaa Arg Arg Xaa Arg Arg Xaa Arg Arg Xaa Arg Xaa Ala
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Muscle-specific Homing Peptide

<400> SEQUENCE: 56

Cys Arg Val Ala Ser Val Leu Pro Cys
1               5

<210> SEQ ID NO 57
<211> LENGTH: 5
<212> TYPE: PRT
<213> ORGANISM: Artificial Sequence
<220> FEATURE:
<223> OTHER INFORMATION: Cell penetrating peptide

<400> SEQUENCE: 57

Arg Arg Arg Arg Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Cell penetrating peptide

<400> SEQUENCE: 58

Arg Arg Arg Arg Arg Gly
1               5

<210> SEQ ID NO 59
<211> LENGTH: 7
<212> TYPE: PRT
<213> ORGANISM: Artificial Sequence
<220> FEATURE:
<223> OTHER INFORMATION: Cell penetrating peptide

<400> SEQUENCE: 59

Arg Arg Arg Arg Arg Arg Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Cell penetrating peptide

<400> SEQUENCE: 60

Arg Arg Arg Arg Arg Arg Arg Gly
1               5

<210> SEQ ID NO 61
<211> LENGTH: 9
```

```
<212> TYPE: PRT
<213> ORGANISM: Artificial Sequence
<220> FEATURE:
<223> OTHER INFORMATION: Cell penetrating peptide

<400> SEQUENCE: 61

Arg Arg Arg Arg Arg Arg Arg Arg Gly
 1               5

<210> SEQ ID NO 62
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 62

Arg Arg Arg Arg Arg Arg Arg Arg Arg Gly
 1               5                  10
```

COMPOUND AND METHOD FOR TREATING MYOTONIC DYSTROPHY

CROSS REFERENCE TO RELATED APPLICATION

This application is a continuation of U.S. application Ser. No. 14/038,314, filed Sep. 26, 2013 (now allowed); which is a continuation of U.S. application Ser. No. 13/101,942, filed May 5, 2011 (abandoned), which is a continuation-in-part of U.S. application Ser. No. 12/493,140, filed Jun. 26, 2009 (abandoned), all of which are incorporated by reference in their entireties.

STATEMENT REGARDING SEQUENCE LISTING

The sequence listing associated with this application is provided in text format in lieu of a paper copy, and is hereby incorporated by reference into the specification. The name of the text file containing the Sequence Listing is $583022_{13}$ SPT-8083CON$3_{13}$ ST25.txt. The text file is about 13,776 bytes, was created on Nov. 9, 2017, and is being submitted electronically via EFS-Web.

FIELD OF THE INVENTION

The present invention relates to antisense oligonucleotides targeted to polyCUG repeats in the 3'UTR region of dystrophia myotonica protein kinase (DMPK) mRNA, and methods for treating myotonic dystrophy DM1.

BACKGROUND OF THE INVENTION

Myotonic dystrophy type 1 (DM1) and type 2 (DM2) are associated with long polyCUG and polyCCUG repeats in the 3'-UTR and intron 1 regions of the transcript dystrophia myotonica protein kinase (DMPK) and zinc finger protein 9 (ZNF9), respectively (Wheeler and Thornton 2007). While normal individuals have as many as 30 CTG repeats, DM1 patients carry a larger number of repeats ranging from 50 to thousands. The severity of the disease and the age of onset correlates with the number of repeats. Patients with adult onsets show milder symptoms and have less than 100 repeats, juvenile onset DM1 patients carry as many as 500 repeats and congenital cases usually have around a thousand CTG repeats. The expanded transcripts containing CUG repeats form a secondary structure, accumulate in the nucleus in the form of nuclear foci and sequester RNA-binding proteins (RNA-BP).

Several RNA-BP have been implicated in the disease, including muscleblind-like (MBNL) proteins and CUG-binding protein (CUGBP). MBNL proteins are homologous to *Drosophila* muscleblind (Mbl) proteins necessary for photoreceptor and muscle differentiation. MBNL and CUGBP have been identified as antagonistic splicing regulators of transcripts affected in DM1 such as cardiac troponin T (cTNT), insulin receptor (IR) and muscle-specific chloride channel (ClC-1).

Myotonic dystrophy type 2 (DM2) is associated with repeats in the first intron of the ZNF9 gene on chromosome 3. CNBP (ZNF9) is the only gene known to be associated with myotonic dystrophy type 2. CNBP intron 1 contains a complex repeat motif, (TG)n(TCTG)n(CCTG)n, and expansion of the CCTG repeat causes DM2. The number of CCTG repeats in expanded alleles can range from approximately 75 to more than 11,000, with a mean of approximately 5000 repeats.

DM1 and DM2 are associated with a variety of serious pathologies including muscle abnormalities and weakness, and in the heart, conduction abnormalities.

SUMMARY OF THE INVENTION

The present invention is based on the unexpected antisense activity of 9-base phosphorodiamidate morpholino oligomers (PMOs), relative, for example, to longer PMOs, for reducing or ameliorating one or more symptoms of myotonic dystrophy type 1 (DM1) or type 2 (DM2). These 9-base antisense oligomers described herein can employ a variety of PMO-based chemistries, including PMO, PMO+, PPMO, and PPMO+ chemistries, as described herein.

Embodiments of the present invention therefore include antisense compounds for treating myotonic dystrophy type 1 (DM1), comprising a morpholino antisense oligonucleotide of 9 bases, where the 9 bases are complementary to poly-CUG repeats in the 3'UTR region of dystrophia myotonica protein kinase (DMPK) mRNA. In certain embodiments, the oligonucleotide is a phosphorodiamidate morpholino oligonucleotide (PMO). In some embodiments, at least one and up to about 1 per every 2 intersubunit linkage(s) of the oligonucleotide contains a pendant cationic group. In specific embodiments, the cationic group comprises an optionally substituted piperazino group (PMO+). In certain embodiments, the oligonucleotide is conjugated to a cell-penetrating peptide, such as an arginine-rich peptide (PPMO or PPMO+).

Also included are methods of treating myotonic dystrophy DM1 in a mammalian subject, comprising administering to the subject, a morpholino antisense compound of 9 bases, where the 9 bases are complementary to polyCUG repeats in the 3'UTR region of dystrophia myotonica protein kinase (DMPK) mRNA, and optionally repeating said administering at least once every one week to 3 months. In some embodiments, at least one and up to about 1 per every 2 intersubunit linkage(s) of the oligonucleotide contains a pendant cationic group. In specific embodiments, the cationic group comprises an optionally substituted piperazino group. In certain embodiments, the oligonucleotide is conjugated to an arginine-rich peptide.

The compounds may be administered by intravenous or subcutaneous injection to the subject, at a dose between 1-5 or 1-20 mg/kg body weight antisense compound, and the administering step may be continued at regular intervals of every two weeks to three months. The subject may be monitored during the treatment for improvement in muscle performance, heart conduction properties, and/or for a reduction in serum creatine kinase.

Certain embodiments include antisense compounds for treating myotonic dystrophy type 2 (DM2), comprising a morpholino antisense oligonucleotide of 9 bases, where the 9 bases are complementary to polyCCUG repeats in the first intron region of zinc finger protein 9 (ZNF9) pre-mRNA. Also included are methods of treating myotonic dystrophy DM1 in a mammalian subject, comprising administering to the subject, a morpholino antisense oligonucleotide of 9 bases, where the 9 bases are complementary to polyCCUG repeats in the first intron region of zinc finger protein 9 (ZNF9) pre-mRNA, and optionally repeating said administering at least once every one week to 3 months.

DETAILED DESCRIPTION

Definitions

Figure 1A:
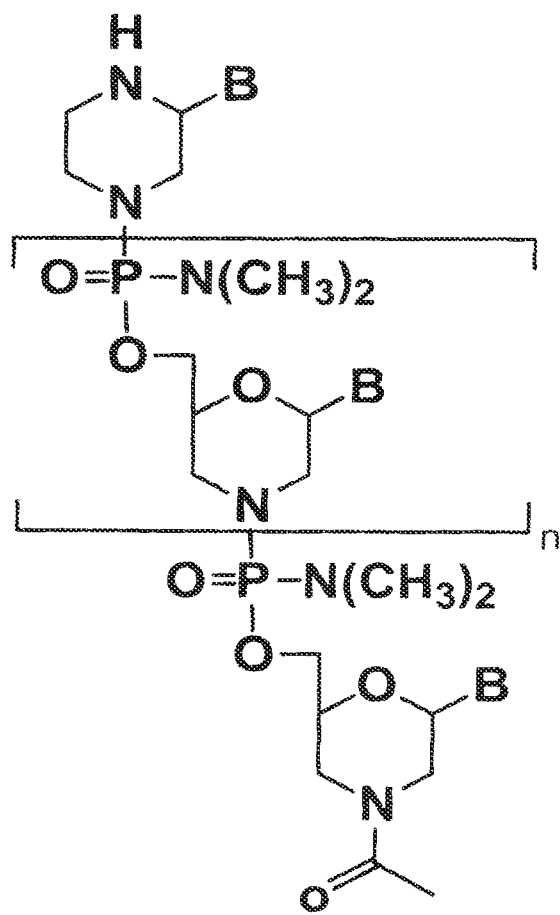
FIGS. 1A-C show exemplary structures of a phosphorodiamidate-linked morpholino oligomer (PMO), a peptide-conjugated PMO (PPMO), and a peptide-conjugated PMO having cationic intersubunit linkages (PPMO+), respectively. Though multiple cationic linkage types are illustrated in FIG. 1C, a PMO+ or PPMO+ oligomer will typically include just one type of cationic linkage.

The terms below, as used herein, have the following meanings, unless indicated otherwise:

The terms "cell penetrating peptide" or "CPP" are used interchangeably and refer to cationic cell penetrating peptides, also called transport peptides, carrier peptides, or peptide transduction domains. Examples of cell-penetrating peptides include arginine-rich peptides. The peptides, as shown herein, typically have the capability of inducing cell penetration within 100% of cells of a given cell culture population and allow macromolecular translocation within multiple tissues in vivo upon systemic administration.

The terms "antisense oligomer" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits are based on ribose or another pentose sugar or, in a preferred embodiment, a morpholino group (see description of morpholino oligomers below). The oligomer may have exact or near sequence complementarity to the target sequence; variations in sequence near the termini of an oligomer are generally preferable to variations in the interior.

In one aspect of the invention, for the treatment of DM1, the antisense oligonucleotide is complementary to at least 8, optionally 9-12 or more contiguous bases in polyCUG repeats within the 3' UTR regions of the transcript for dystrophia myotonica protein kinase (DMPK) in muscle cells, and is designed to bind by hybridization to these repeats, blocking binding of splice-associated proteins, such as one or more muscleblind family proteins, e.g., MBNL1, or CUGBP to the transcript. The oligonucleotide may be said to be "directed to" or "targeted against" 3'UTR polyCUG repeats with which it hybridizes. The target sequence may include a polyCUG region of at least 8 contiguous bases, preferably at least 9-25, and up to 40 bases or more.

In another aspect of the invention, for the treatment of DM2, the antisense oligonucleotide is complementary to at least 8, optionally 9-12 or more contiguous bases in polyCUG repeats within intron 1 of the pre-mRNA transcript for zinc finger protein 9 (ZNF9) in muscle cells, and is designed to bind by hybridization to these repeats, blocking binding of splice-associated proteins, such as one or more muscleblind family proteins, e.g., MBNL1, or CUGBP to the pre-mRNA transcript or the excised intron 1 resulting from ZNF9 pre-mRNA processing. The oligonucleotide may be said to be "directed to" or "targeted against" polyCCUG repeats with which it hybridizes. The target sequence may include a polyCCUG region of at least 8 contiguous bases, preferably at least 9-25, and up to 40 bases or more.

Specific embodiments include 9 base antisense oligomers such as PMO, PMO+, PPMO, or PPMO+ antisense oligonucleotides/compounds that are fully complementary to polyCUG repeats within the 3' UTR regions of the RNA transcript for DMPK, and antisense oligonucleotides/compounds that are fully complementary to polyCCUG repeats within intron 1 of the pre-mRNA transcript for ZNF9. Examples include the antisense oligomers of SEQ ID NOS: 1, 5, 9, and 15-18 targeted to polyCUG repeats, and SEQ ID NOS: 19, 21, 23, 26-29 targeted to polyCCUG repeats.

The terms "morpholino oligomer" or "PMO" (phosphoramidate- or phosphorodiamidate morpholino oligomer) refer to an oligonucleotide composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide. See, for example, the structure in FIG. 1A, which shows a preferred phosphorodiamidate linkage type. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Pubn. No. WO 2008036127 (cationic linkages), all of which are incorporated herein by reference.

An "amino acid subunit" or "amino acid residue" can refer to an α-amino acid residue (—CO—CHR—NH—) or a β- or other amino acid residue (e.g. —CO—(CH$_2$)$_n$CHR—NH—), where R is a side chain (which may include hydrogen) and n is 1 to 6, preferably 1 to 4.

The term "naturally occurring amino acid" refers to an amino acid present in proteins found in nature. The term "non-natural amino acids" refers to those amino acids not present in proteins found in nature, examples include beta-alanine (β-Ala), 6-aminohexanoic acid (Ahx) and 6-aminopentanoic acid.

A "marker compound" refers to a detectable compound attached to a transport peptide for evaluation of transport of the resulting conjugate into a cell. The compound may be visually or spectrophotometrically detected, e.g. a fluorescent compound or fluorescently labeled compound, which may include a fluorescently labeled oligomer. Preferably, the marker compound is a labeled or unlabeled antisense oligomer. In this case, detection of transport involves detection of a product resulting from modulation of splicing and/or transcription of a nucleic acid by an antisense oligomeric compound. Exemplary methods, such as a splice correction assay or exon skipping assay, are described in Materials and Methods below.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

The terms "antisense compound" or "compound" or "conjugate compound" include stand-alone antisense oligonucleotides (e.g., PMO, PMO+), and compounds formed by conjugating a cell-penetrating peptide (e.g., arginine-rich peptide) to an antisense oligonucleotide (e.g., PPMO, PPMO+). Examples of arginine-rich peptides include SEQ ID NOS:30-44, including the (RXRR(X/B)R)$_2$XB (SEQ ID NO:55) cell-penetrating peptides, which can be conjugated, for example, to an oligonucleotide targeted against a region of polyCUG or polyCCUG repeats.

"Systemic administration" of a compound refers to administration, such as intravenous (iv) subcutaneous (subQ), intramuscular (IM), and intraperitoneal (IP) that delivers the compound directly into the bloodstream.

A systemically administered antisense oligonucleotide can be targeted, for example, to heart muscle tissue by conjugation to the CPP (RXRRBR)$_2$ (SEQ ID NO:42) with an XB linkage, or other cell-penetrating peptide. In certain instances, the compound, when administered systemically to a DM1 subject in accordance with the method herein, produces a measurable improvement in heart muscle performance and/or improvement in conduction properties of the heart, as measured by known methods.

Structural Features of Transport Peptides

Exemplary cell-penetrating peptides that can employed in the invention include a class of a transport peptide having 8 to 30 amino acid residues in length and consisting of subsequences selected from the group consisting of RXR, RX, RB, and RBR; where R is arginine (which may include D-arginine, represented in the sequences herein by r), B is β-alanine, and each X is independently —C(O)—(CHR$^1$)$_n$—NH—, where n is 4-6 and each R$^1$ is independently H or methyl, such that at most two R$^1$'s are methyl. Preferably, each R$^1$ is hydrogen. These peptides have the generic formula (RXRR(B/X)R)$_2$XB (SEQ ID NO:55), where R is arginine; B is β-alanine; and each X is —C(O)—(CH$_2$)$_n$—NH—, where n is 4-6, preferably 6, and include both (RXRRBR)$_2$ (SEQ ID NO:42) with an XB linkage, and (RXRRXR)$_2$ (SEQ ID NO:40) with an XB linkage, and where R is arginine; B is β-alanine; and each X is —C(O)—(CH$_2$)$_n$—NH—, where n is 4-6. As discussed below, these peptides have been discovered to selectively target an oligonucleotide, including a PMO, to muscle tissue, including heart muscle tissue.

Table 1 below includes certain transport peptides in this class that have been evaluated, in conjugation with suitable antisense oligonucleotides, for their ability to selectively target various tissues, including heart and skeletal muscle. See, e.g., U.S. application Ser. No. 12/493,140, incorporated by reference in its entirety. The peptides have been evaluated for cellular uptake, as determined by flow cytometry; for antisense activity, as determined by a splice correction assay (Kang, Cho et al. 1998); and for cellular toxicity, as determined by MTT cell viability, propidium iodide membrane integrity and hemolysis assays, and microscopic imaging, and their uptake and functional activity in muscle tissue relative to a variety of non-muscle tissue were compared. The (RXRRXR)$_2$ peptide (SEQ ID NO:40) with an XB linkage was among the most active in antisense activity, as determined by the splice correction assay, both in the presence and absence of added serum. Both (RXRR(B/X)R)$_2$XB (SEQ ID NO:55) peptides were effective in selectively targeting oligonucleotides to heart and skeletal tissue, while showing relatively low-level targeting to a variety of other tissues, including mammary gland tissue, ovary/prostate (particularly (RXRRXR)$_2$ (SEQ ID NO:40) with an XB linkage), and brain. Embodiments of the present invention may employ any one or more of these cell-penetrating or arginine-rich peptides.

TABLE 1

Cell-Penetrating Peptides

| Name (Designation) | Sequence | SEQ ID NO.[a] |
|---|---|---|
| rTAT | RRRQRRKKR | 30 |
| Tat | RKKRRQRRR | 31 |
| R$_9$F$_2$ | RRRRRRRRRFF | 32 |
| R$_5$F$_2$R$_4$ | RRRRRFFRRRR | 33 |
| R$_4$ | RRRR | 34 |
| R$_5$ | RRRRR | 35 |
| R$_6$ | RRRRRR | 36 |
| R$_7$ | RRRRRRR | 37 |
| R$_8$ | RRRRRRRR | 38 |
| R$_9$ | RRRRRRRRR | 39 |
| (RAhxR)$_4$; (P007) | RAhxRRAhxRRAhxRRAhxR | 40 |
| (RAhxR)$_5$; (CP04057) | RAhxRRAhxRRAhxRRAhxRRAhxR | 41 |
| (RAhxRRBR)$_2$; (CP06062) | RAhxRRBRRAhxRRBR | 42 |
| (RAR)$_4$F$_2$ | RARRARRARRARFFC | 43 |
| (RGR)$_4$F$_2$ | RGRRGRRGRRGRFFC | 44 |

[a]Sequences assigned to SEQ ID NOs do not include the linkage portion (e.g., C, G, Ahx, B, AhxB where Ahx and B refer to 6-aminohexanoic acid and beta-alanine, respectively).

Therapeutic Applications

The phosphorodiamidate morpholino oligomers (e.g., PMO, PMO+) and other antisense oligomers described herein are useful for treating myotonic dystrophy type 1 (DM1), and the conjugate compounds (e.g., PPMO, PPMO+) of the present invention are further useful for targeting and delivering these antisense oligomers across both the cell and nuclear membranes to the nucleus of muscle cells in skeletal and heart muscle tissue, by exposing the cell to an antisense oligomer or conjugate comprising the oligomer covalently linked to a carrier peptide, as described herein.

Treatment of Myotonic Dystrophy. As the name of the disorder implies, the characteristic clinical manifestation in DM is myotonia (muscle hyperexcitability) and muscle degeneration. Affected individuals will also develop insulin resistance, cataracts, heart conduction defects, testicular atrophy, hypogammaglobulinemia and sleep disorders. Symptoms of DM can manifest in the adult or in childhood. The childhood onset form of the disease is often associated with mental retardation. In addition, there is a form of the disease referred to as congenital myotonic dystrophy. This latter form of the disease is frequently fatal and is seen almost exclusively in children born of mothers who themselves are mildly affected by the disease. In congenital DM the facial manifestations are distinctive due to bilateral facial palsy and marked jaw weakness. Many infants with congenital DM die due to respiratory insufficiency before a proper diagnosis of the disease is made.

DM1 initially involves the distal muscles of the extremities and only as the disease progresses do proximal muscles become affected. In addition, muscles of the head and neck are affected early in the course of the disease. Weakness in eyelid closure, limited extraocular movement and ptosis results from involvement of the extraocular muscles. Many individuals with DM1 exhibit a characteristic "haggard" appearance that is the result of atrophy of the masseters (large muscles that raise and lower the jaw), sternocleidomastoids (large, thick muscles that pass obliquely across each side of the neck and contribute to arm movement) and the temporalis muscle (muscle involved in chewing).

Treatment of DM1, in accordance with general embodiments of the invention, may comprise, for example: (i) administering to the subject with DM1, an antisense compound comprising an antisense oligonucleotide having 8-30 bases, with at least 8 contiguous bases being complementary to the polyCUG repeats in the 3'UTR region of dystrophia myotonica protein kinase (DMPK) mRNA in DM1 and optionally conjugated to the oligonucleotide, a cell-penetrating peptide, and (ii) optionally repeating the compound administration at least once every one week to once every three months or longer. Examples of cell-penetrating peptides include the peptides of SEQ ID NOS:30-44. In specific embodiments, the cell-penetrating peptide may have the sequence (RXRR(B/X)R)$_2$XB (SEQ ID NO:55), where R is arginine; B is β-alanine; and each X is —C(O)—(CH$_2$)$_n$—NH—, where n is 4-6.

Treatment of DM1, in accordance with specific embodiments of the invention, may comprise: (i) administering to the subject with DM1 a 9-base morpholino antisense oligonucleotide, where the 9 bases are complementary to polyCUG repeats in the 3'UTR region of dystrophia myotonica protein kinase (DMPK) mRNA, and (ii) optionally repeating said administering at least once every one week to 3 months. The morpholino antisense oligomer may be a phosphorodiamidate morpholino oligonucleotide (PMO), and/or it may be a PMO where at least one and up to about 1 per every 2 intersubunit linkage(s) contains a pendant cationic group, such as an optionally piperazino group (PMO+). The PMO or PMO+ compound may be optionally conjugated to a cell-penetrating peptide, such as an arginine-rich peptide (e.g., PPMO, PPMO+).

The compound is preferably administered by intravenous or subcutaneous injection to the subject, at a dose between 1-5 or 1-20 mg/kg body weight antisense compound, at a dosing schedule of once a month to once every 2-3 months. For subQ administration, the dose required may be roughly twice that for IV administration. During the course of treatment, the patient is monitored for improvement or stabilization of muscle performance, improvement in heart conduction properties and/or reduction in serum reduction in serum creatine kinase. Because myotonic dystrophy is a chronic disease, the treatment method will be applied over the subject's lifetime, with dose adjustments being made during the treatment period to achieve a desired level of muscle function and to accommodate patient growth.

The treatment methods offer a number of important advantages over earlier proposed antisense methods of treating DM1. First, targeting, uptake and antisense activity of the antisense compounds described herein into skeletal muscle, heart muscle, or both, is efficient. This allows effective treatment with relatively modest compound doses, e.g., in the range 1-5 mg/kg subject weight. Second, little or no compound toxicity has been observed, as evidenced, for example, by no microscopically observable increases in muscle damage, inflammatory cellular infiltrates, or necrotic fibers in muscles injected with PPMOs and/or PMOs. Finally, in certain instances, the effect of a single dose may be effective for up to three months or more, allowing the patient to be effectively treated by dosing at intervals of no less than one month, and up to 3 months or more between successive treatments.

Combination with Homing Peptides

The antisense oligonucleotides and conjugate compounds of the invention may be used in conjunction with homing peptides selective for the target tissue, to further enhance muscle-specific delivery. An example of this approach can be found in the application of muscle-binding peptides (Samoylova and Smith, 1999; Vodyanoy et al., U.S. Appn. Pubn. No. 20030640466) coupled to antisense oligomers designed to be therapeutic treatments for Duchenne muscular dystrophy (DMD) (Gebski, Mann et al. 2003; Alter, Lou et al. 2006) (PCT Pubn. No. WO2006000057). The heptapeptide sequence ASSLNIA (SEQ ID NO:45) has enhanced in vivo skeletal and cardiac muscle binding properties, as described by Samoylova and Smith. As a further example, a pancreas-homing peptide, CRVASVLPC (SEQ ID NO:56), mimics the natural prolactin receptor ligand (Kolonin, Sun et al. 2006).

An exemplary dual peptide molecule has a cell penetrating peptide to one terminus, e.g. at the 5' end of the antisense oligomer, as described herein, and a homing peptide coupled to the other terminus, i.e. the 3' terminus. The homing peptide localizes the peptide-conjugated PMO to the target tissue, where the cell-penetrating peptide moiety effects transport into the cells of the tissue.

Alternatively, a preferred exemplary dual peptide molecule would have both a homing peptide (HP) and cell-penetrating peptide (CPP) conjugated to one end, e.g. the 5' terminus of the antisense oligomer, in either a HP-CPP-PMO configuration or, more preferably, a CPP-HP-PMO configuration.

TABLE 2

Examples of Muscle-specific Homing Peptides (HP)

| Target Tissue | Peptide Sequence (NH$_2$ to COOH) | SEQ ID NO. |
|---|---|---|
| Skeletal Muscle - SMP1 | ASSLNIA | 45 |
| SMP2 | SLGSFP | 46 |
| SMP3 | SGASAV | 47 |
| SMP4 | GRSGAR | 48 |
| SMP5 | TARGEHKEEELI | 49 |
| Cardiac Muscle - CMP1 | WLSEAGPVVTVRALRGTGSW | 50 |
| CMP2 | VTVRALRGTSW | 51 |
| CMP3 | VVTVRALRGTGSW | 52 |
| CMP4 | CRPPR | 53 |
| CMP5 | SKTFNTHPQSTP | 54 |
|  | CRVASVLPC | 56 |

Peptide-Antisense Oligomer Conjugate Compositions
Conjugates for Specific Muscle Treatments Therapeutic conjugates comprising selected transport peptide sequences are also provided by the invention. These include conjugates comprising a carrier peptide (RXRR(B/X)R)$_2$XB (SEQ ID NO:55), as described herein, conjugated to an oligonucleotide, e.g., PMO, designed for therapeutic action within muscle tissue. Also included are conjugates comprising an oligonucleotide conjugated to any one of SEQ ID NOS:30-44.

The conjugates may further comprise a targeting moiety effective to bind to tissue specific receptors of a target tissue type, linked to the therapeutic compound or, preferably, to another terminus of the carrier peptide. In particularly preferred embodiments, a homing peptide such as described above is conjugated to therapeutic compound or to the cell-penetrating peptide.

For use in treating myotonic dystrophy DM1, the conjugate compound may comprise an antisense oligonucleotide, having 8-30 bases, preferably 9 bases, with at least 8 or 9 or more contiguous bases being complementary to the poly-CUG repeats in the 3'UTR region of dystrophia myotonica protein kinase (DMPK) mRNA, and conjugated to the oligonucleotide, a cell-penetrating peptide of any one of SEQ ID NOS:30-44, including, for example, a peptide having the sequence (RXRR(B/X)R)$_2$XB (SEQ ID NO:55), where R is arginine; B is β-alanine; and each X is —C(O)—(CH$_2$)$_n$—NH—, where n is 4-6. Such compounds are effective to selectively block the sequestration of muscleblind-like 1 protein (MBNL1) and/or CUGBP in heart and quadricep muscle in a myotonic dystrophy animal model.

Morpholino Oligomers Having Cationic and Other Intersubunit Linkages

In preferred embodiments, as noted above, the antisense oligomer is a phosphorodiamidate morpholino oligonucleotide (PMO). Certain PMOs may include between about 10-50% or 20-50% positively charged or cationic backbone linkages, as described below and further in WO/2008/036127, which is incorporated by reference.

Figure 1B:
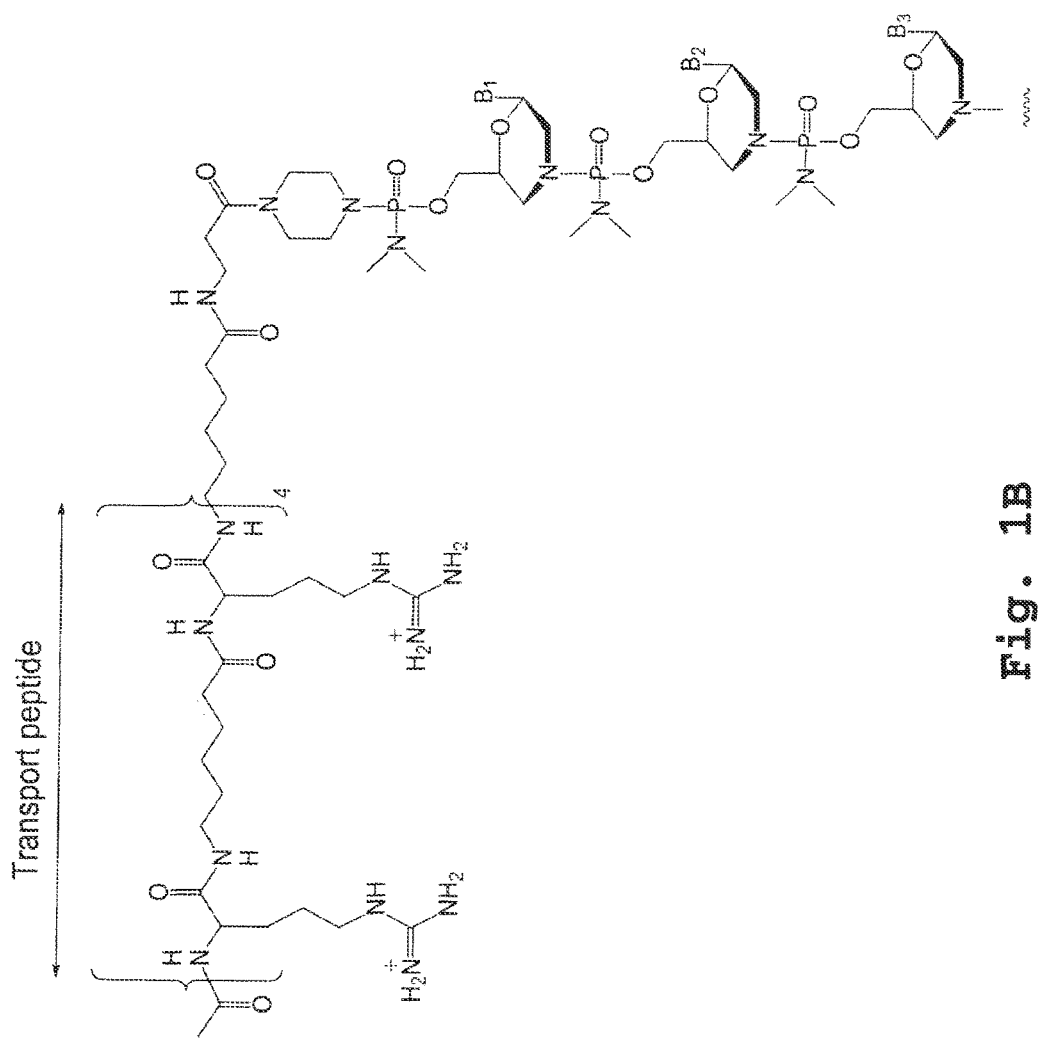
Figure 1C:
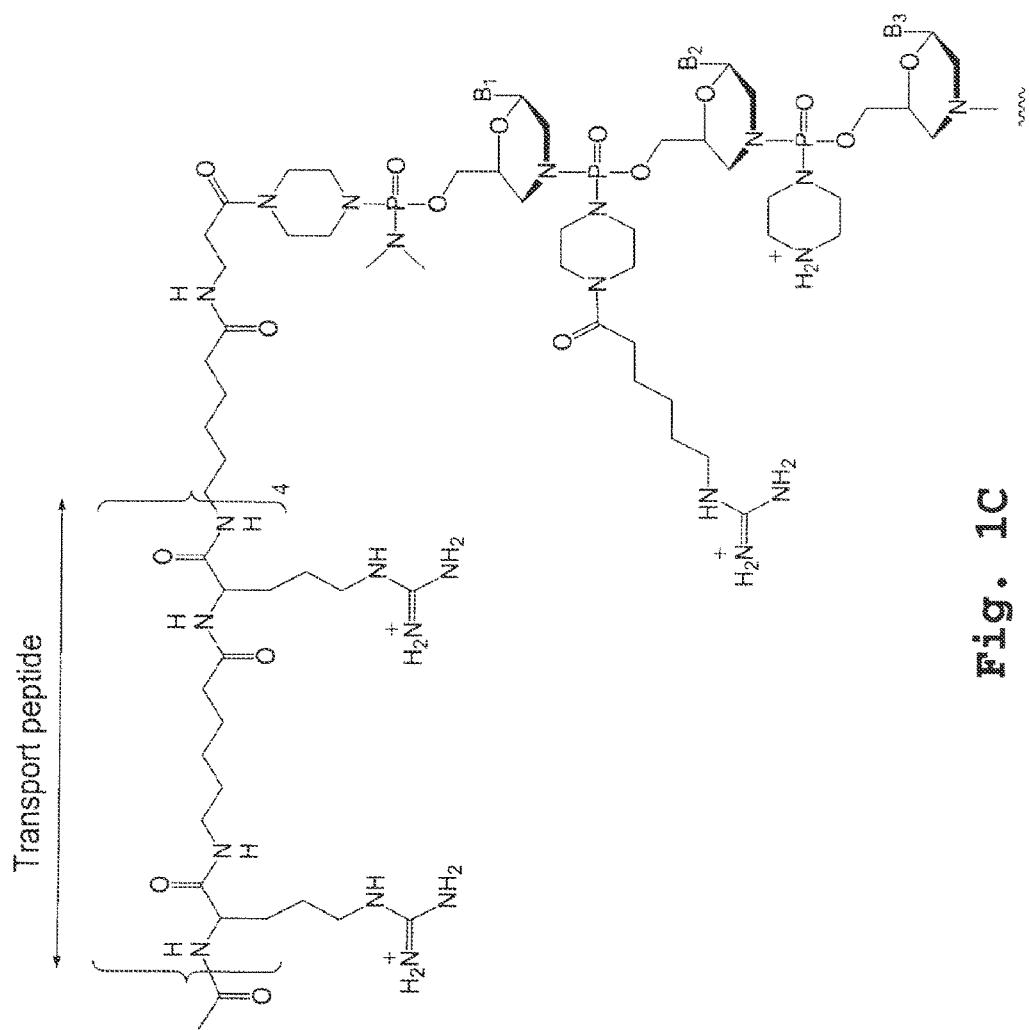

Certain cationic PMOs (e.g., PMO+) include morpholino oligomers in which at least one intersubunit linkage between two consecutive morpholino ring structures contains a pendant cationic group. The pendant group bears a distal nitrogen atom that can bear a positive charge at neutral or near-neutral (e.g., physiological) pH. Examples are shown in FIGS. 1B-C.

The intersubunit linkages in these oligomers are preferably phosphorus-containing linkages, having the structure:

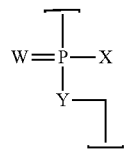

where
W is S or O, and is preferably O,
X=NR$^1$R$^2$ or OR$^6$,
Y=O or NR$^7$,
and each said linkage in the oligomer is selected from:
(a) uncharged linkage (a), where each of R$^1$, R$^2$, R$^6$ and R$^7$ is independently selected from hydrogen and lower alkyl;
(b1) cationic linkage (b1), where X=NR$^1$R$^2$ and Y=O, and NR$^1$R$^2$ represents an optionally substituted piperazino group, such that R$^1$R$^2$=—CHRCHRN(R$^3$)(R$^4$)CHRCHR—, where
each R is independently H or CH$_3$,
R$^4$ is H, CH$_3$, or an electron pair, and
R$^3$ is selected from H, lower alkyl, e.g. CH$_3$, C(=NH)NH$_2$, Z-L-NHC(=NH)NH$_2$, and {C(O)CHR'NH}$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;

(b2) cationic linkage (b2), where X=NR$^1$R$^2$ and Y=O, R$^1$=H or CH$_3$, and R$^2$=LNR$^3$R$^4$R$^5$, where L, R$^3$, and R$^4$ are as defined above, and R$^5$ is H, lower alkyl, or lower (alkoxy)alkyl; and (b3) cationic linkage (b3), where Y=NR$^7$ and X=OR$^6$, and R$^7$=LNR$^3$R$^4$R$^5$, where L, R$^3$, R$^4$ and R$^5$ are as defined above, and R$^6$ is H or lower alkyl;

and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 80%, 10% to 50%, or 10% to 35% of the linkages may be cationic linkages.

In one embodiment, at least one linkage is of type (b1), where, preferably, each R is H, R$^4$ is H, CH$_3$, or an electron pair, and R$^3$ is selected from H, lower alkyl, e.g. CH$_3$, C(=NH)NH$_2$, and C(O)-L-NHC(=NH)NH$_2$. The latter two embodiments of R$^3$ provide a guanidino moiety, either attached directly to the piperazine ring, or pendant to a linker group L, respectively. For ease of synthesis, the variable Z in R$^3$ is preferably C(O)(carbonyl), as shown.

The linker group L, as noted above, contains bonds in its backbone selected from alkyl (e.g. —CH$_2$—CH$_2$—), alkoxy (—C—O—), and alkylamino (e.g. —CH$_2$—NH—), with the proviso that the terminal atoms in L (e.g., those adjacent to carbonyl or nitrogen) are carbon atoms. Although branched linkages (e.g. —CH$_2$—CHCH$_3$—) are possible, the linker is preferably unbranched. In one embodiment, the linker is a hydrocarbon linker. Such a linker may have the structure —(CH$_2$)$_n$—, where n is 1-12, preferably 2-8, and more preferably 2-6.

The use of embodiments of linkage types (b1), (b2) and (b3) above to link morpholino subunits may be illustrated graphically as follows:

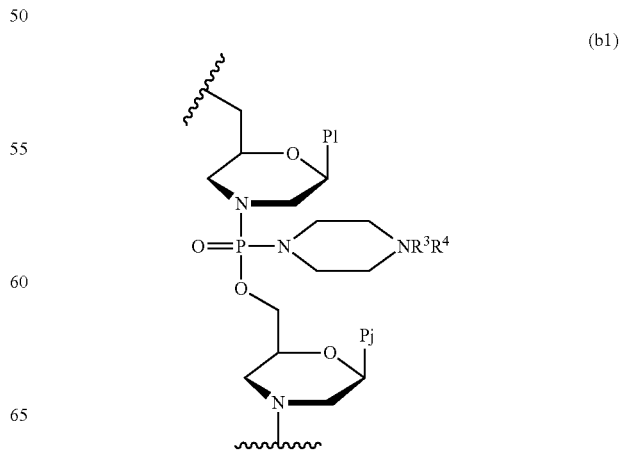

-continued

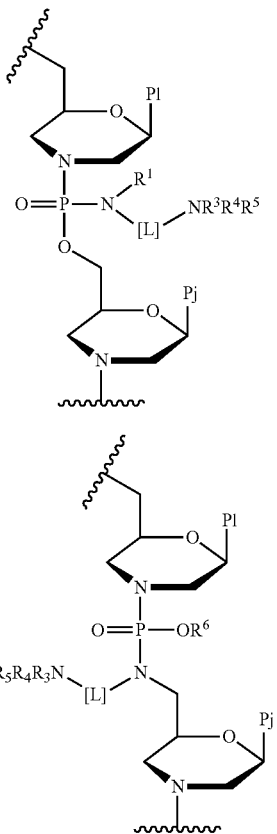

Preferably, all cationic linkages in the oligomer are of the same type; i.e. all of type (b1), all of type (b2), or all of type (b3). The base-pairing moieties Pi may be the same or different, and are generally designed to provide a sequence which binds to a target nucleic acid.

In further embodiments, the cationic linkages are selected from linkages (b1') and (b1") as shown below, where (b1') is referred to herein as a "Pip" linkage and (b1") is referred to herein as a "GuX" linkage:

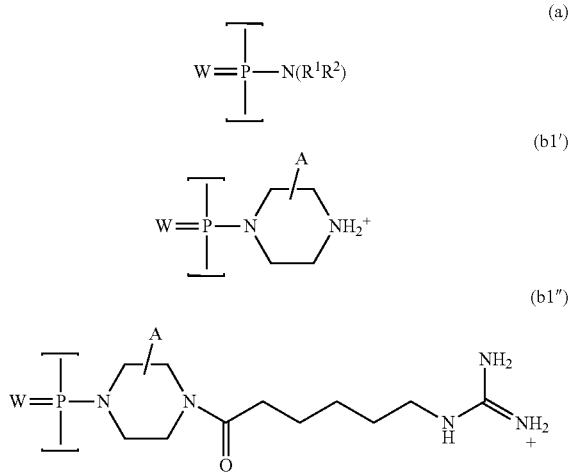

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 20% to 80%, 20% to 50%, or 20% to 30% of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

Oligomers having any number of cationic linkages can be used, including fully cationic-linked oligomers. Preferably, however, the oligomers are partially charged, having, for example, 5, 10, 20, 30, 40, 50, 60, 70, 80 or 90 percent cationic linkages. In selected embodiments, about 10 to 80, 20 to 80, 20 to 60, 20 to 50, 20 to 40, or about 20 to 35 percent of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 15 to 25 subunits. For example, a cationic oligomer having 19-20 subunits, a useful length for an antisense oligomer, may ideally have two to seven, e.g. four to six, or three to five, cationic linkages, and the remainder uncharged linkages. An oligomer having 14-15 subunits may ideally have two to five, e.g. 3 or 4, cationic linkages and the remainder uncharged linkages. Specific examples include a 9 subunit oligomer with about 1, 2, or 3 cationic linkages, and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

As noted above, the substantially uncharged oligonucleotide may be modified to include one or more charged linkages, e.g. up to about 1 per every 2-5 uncharged linkages, typically 3-5 per every 10 uncharged linkages. Optimal improvement in antisense activity is seen where up to about half of the backbone linkages are cationic. Some, but not maximum enhancement is typically seen with a small number e.g., 10-20% cationic linkages; where the number of cationic linkages exceeds 50-60%, the sequence specificity of the antisense binding to its target may be compromised or lost.

The enhancement seen with added cationic backbone charges may, in some case, be further enhanced by distributing the bulk of the charges close of the "center-region" backbone linkages of the antisense oligonucleotide, e.g., in a 20-mer oligonucleotide with 8 cationic backbone linkages, having 70%-100% of these charged linkages localized in the 10 centermost linkages.

Other Oligomer Types

Delivery of alternative antisense chemistries can also benefit from the disclosed carrier peptide. Specific examples of other antisense compounds useful in this invention include those in which at least one, or all, of the internucleotide bridging phosphate residues are modified phosphates, such as methyl phosphonates, phosphorothioates, or phosphoramidates. Also included are molecules wherein at least one, or all, of the nucleotides contains a 2' lower alkyl moiety (e.g., C1-C4, linear or branched, saturated or unsaturated alkyl, such as methyl, ethyl, ethenyl, propyl, 1-propenyl, 2-propenyl, or isopropyl).

In other oligonucleotide mimetics, both the sugar and the internucleoside linkage, i.e., the backbone, of the nucleotide units are modified. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-phosphate backbone of an oligonucleotide is replaced with an amide containing backbone, in particular an aminoethylglycine backbone.

Modified oligonucleotides may be classified as "chimeric," e.g., containing at least one region wherein the oligonucleotide is modified so as to confer increased resistance to nuclease degradation or increased cellular uptake, and an additional region for increased binding affinity for the target nucleic acid.

EXAMPLES

The following examples are intended to illustrate but not to limit the invention.

Example 1

PMO, PMO+, PPMO and PPMO+ Consisting of (CAG)n Repeats Reverse Molecular and Physiological Manifestations of DM1 in a Mouse Model To determine whether antisense compositions described herein (e.g., SEQ ID NOs: 1-18) can influence in vivo expanded CUG (CUGexp) repeat interactions with MBNL1 splicing factor, their effects can be examined in a transgenic mouse model of DM1. The antisense oligonucleotides and conjugates shown in Table A below can be manufactured according to routine techniques and then tested in this transgenic mouse model of DM1.

TABLE A

PMO, PMO+, PPMO, and PPMO+ agents targeted to polyCUG repeats in the 3'UTR region of dystrophia myotonica protein kinase (DMPK).

| Sample Name | Sequence | 5'End | 3'End |
| --- | --- | --- | --- |
| CAG 9mer | CAG CAG CAG (SEQ ID NO: 1) | EG3 | H |
| CAG 9mer-B | CAG CAG CAG (SEQ ID NO: 1) | EG3 | CP06062 |
| CAG 9mer-R9F2 | CAG CAG CAG (SEQ ID NO: 1) | EG3 | R9F2 |
| CAG 9mer-rTat | CAG CAG CAG (SEQ ID NO: 1) | EG3 | rTat |
| CAG 12mer | CAG CAG CAG CAG (SEQ ID NO: 2) | EG3 | H |
| CAG 12mer-B | CAG CAG CAG CAG (SEQ ID NO: 2) | EG3 | CP06062 |
| CAG 15mer | CAG CAG CAG CAG CAG (SEQ ID NO: 3) | EG3 | H |
| CAG 15mer-B | CAG CAG CAG CAG CAG (SEQ ID NO: 3) | EG3 | CP06062 |
| CAG 18mer | CAG CAG CAG CAG CAG CAG (SEQ ID NO: 4) | EG3 | H |
| CAG 18mer-B | CAG CAG CAG CAG CAG CAG (SEQ ID NO: 4) | EG3 | CP06062 |
| AGC 9mer | AGC AGC AGC (SEQ ID NO: 5) | EG3 | H |
| AGC 9mer-B | AGC AGC AGC (SEQ ID NO: 5) | EG3 | CP06062 |
| AGC 12mer | AGC AGC AGC AGC (SEQ ID NO: 6) | EG3 | H |
| AGC 12mer-B | AGC AGC AGC AGC (SEQ ID NO: 6) | EG3 | CP06062 |
| AGC 15mer | AGC AGC AGC AGC AGC (SEQ ID NO: 7) | EG3 | H |
| AGC 15mer-B | AGC AGC AGC AGC AGC (SEQ ID NO: 7) | EG3 | CP06062 |
| AGC 18mer | AGC AGC AGC AGC AGC AGC (SEQ ID NO: 8) | EG3 | H |
| AGC 18mer-B | AGC AGC AGC AGC AGC AGC (SEQ ID NO: 8) | EG3 | CP06062 |

TABLE A-continued

PMO, PMO+, PPMO, and PPMO+ agents targeted to polyCUG repeats in the 3'UTR region of dystrophia myotonica protein kinase (DMPK).

| Sample Name | Sequence | 5'End | 3'End |
|---|---|---|---|
| GCA 9mer | GCA GCA GCA (SEQ ID NO: 9) | EG3 | H |
| GCA 9mer-B | GCA GCA GCA (SEQ ID NO: 9) | EG3 | CP06062 |
| GCA 12mer | GCA GCA GCA GCA (SEQ ID NO: 10) | EG3 | H |
| GCA 12mer-B | GCA GCA GCA GCA (SEQ ID NO: 10) | EG3 | CP06062 |
| GCA 15mer | GCA GCA GCA GCA GCA (SEQ ID NO: 11) | EG3 | H |
| GCA 15mer-B | GCA GCA GCA GCA GCA (SEQ ID NO: 11) | EG3 | CP06062 |
| GCA 18mer | GCA GCA GCA GCA GCA GCA (SEQ ID NO: 12) | EG3 | H |
| GCA 18mer-B | GCA GCA GCA GCA GCA GCA (SEQ ID NO: 12) | EG3 | CP06062 |
| AGC 25mer | AGC AGC AGC AGC AGC AGC AGC AGC A (SEQ ID NO: 13) | EG3 | H |
| AGC 25mer-B | AGC AGC AGC AGC AGC AGC AGC AGC A (SEQ ID NO: 13) | EG3 | CP06062 |
| CAG 25mer | CAG CAG CAG CAG CAG CAG CAG CAG C (SEQ ID NO: 14) | EG3 | H |
| CAG 25mer-B | CAG CAG CAG CAG CAG CAG CAG CAG C (SEQ ID NO: 14) | EG3 | CP06062 |
| CAG 25mer-R9F2 | CAG CAG CAG CAG CAG CAG CAG CAG C (SEQ ID NO: 14) | EG3 | R9F2 |
| CAG 25mer-rTat | CAG CAG CAG CAG CAG CAG CAG CAG C (SEQ ID NO: 14) | EG3 | rTat |
| CAG 9mer+ | C+AG C+AG C+AG (SEQ ID NO: 15) | EG3 | H |
| CAG 9mer+B | C+AG C+AG C+AG (SEQ ID NO: 15) | EG3 | CP06062 |
| CAG 9mer+ | C+AG CAG CAG (SEQ ID NO: 16) | EG3 | H |
| CAG 9mer+ | CAG CAG C+AG (SEQ ID NO: 17) | EG3 | H |
| CAG 9mer+ | CAG C+AG CAG (SEQ ID NO: 18) | EG3 | H |

*The linkage(s) between the oligonucleotide and the cell-penetrating peptide can included a variety of linkages, but preferred linkages are C, AhxB, G, and B.

$HSA^{LR}$ transgenic mice express human skeletal actin transcripts that have (CUG)250 inserted in the 3' UTR (Mankodi, Logigian et al. 2000). These mice accumulate CUGexp RNA and MBNL1 protein in nuclear foci in skeletal muscle, a process that depends on CUGexp-MBNL1 interaction (Dansithong, Paul et al. 2005). The effect of antisense compositions of the present invention can be examined in their ability to block foci development in muscle cells. PMO and PPMO can be delivered intravenously or intraperitoneally at doses ranging from 30 to 600 micrograms. Muscle tissue can be examined 1-3 weeks later by fluorescence in situ hybridization using probes that hybridize to the CUG repeat or to sequences flanking the repeat. Activity of any given compound can be measured by the magnitude of reduction of nuclear foci and redistribution of MBNL1 from a punctate pattern to diffuse localization in the nucleus.

Compositions of the present invention can also reverse the biochemical consequences of MBNL1 sequestration. Accumulation of CUGexp RNA-MBNL1 complexes in the foci results also in aberrant mis-splicing of several genes, namely, ClC-1, Serca-1, m-Titin, Tnnt3 and Zasp genes (Mulders, van den Broek et al. 2009). $HSA^{LR}$ transgenic mice show alternative splicing changes similar to those observed in human DM1 (Wheeler, Sobczak et al. 2009). DM1-affected, aberrantly spliced exons can be examined in mice treated with compositions of the invention to determine whether alternative splicing is corrected at three weeks following injection of compositions of the present invention. Effects of PMO or PPMO treatment on aberrant splicing can be expected to persist for at least fourteen weeks.

It is also expected that compositions of the present invention can rescue the physiological effects of DM1 (myotonia) and can be examined by measuring the expression and function of chloride channel 1 (ClC-1) which is inactivated by mis-splicing in DM1 and the $HSA^{LR}$ mouse model. Myotonia can be measured through determination of delayed muscle relaxation and repetitive action potentials and are expected to improve in $HSA^{LR}$ mice treated with compositions of the present invention.

Example 2

PMO, PPMOPlus, PPMO and PMO-X Consisting of (CCAG)N Repeats Reverse Molecular and Physiological Manifestations of DM2

To determine whether antisense compositions described herein (e.g., SEQ ID NOs: 19-29) can influence in vivo expanded CCUG (CCUGexp) repeat interactions with MBNL1 splicing factor, their effects can be examined in an analogous transgenic mouse model to that described above for DM1. The antisense oligonucleotides and conjugates shown in Table B below can be manufactured according to routine techniques and then tested in this transgenic mouse model of DM2. The expected experimental outcomes are similar to those described for DM1 in Example 1.

TABLE B

PMO, PMO+, PPMO, and PPMO+ agents targeted to polyCCUG repeats in the first intron of zinc finger protein 9 (ZNF9) pre-mRNA.

| Sample Name | Sequence | 5'End | 3'End |
|---|---|---|---|
| CAGG 9mer | CAG GCA GGC (SEQ ID NO: 19) | EG3 | H |
| CAGG 9mer-B | CAG GCA GGC (SEQ ID NO: 19) | EG3 | CP06062 |
| CAGG 9mer-R9F2 | CAG GCA GGC (SEQ ID NO: 19) | EG3 | R9F2 |
| CCAG 9mer-rTat | CAG GCA GGC (SEQ ID NO: 19) | EG3 | rTat |
| CCAG 12mer | CAG GCA GGC AGG (SEQ ID NO: 20) | EG3 | H |
| CCAG 12mer-B | CAG GCA GGC AGG (SEQ ID NO: 20) | EG3 | CP06062 |
| AGCC 9mer | AGG CAG GCA (SEQ ID NO: 21) | EG3 | H |
| AGCC 9mer-B | AGG CAG GCA (SEQ ID NO: 21) | EG3 | CP06062 |
| AGCC 12mer | AGG CAG GCA GGC (SEQ ID NO: 22) | EG3 | H |
| AGCC 12mer-B | AGG CAG GCA GGC (SEQ ID NO: 22) | EG3 | CP06062 |
| GCCA 9mer | GGC AGG CAG (SEQ ID NO: 23) | EG3 | H |
| GCCA 9mer-B | GGC AGG CAG (SEQ ID NO: 23) | EG3 | CP06062 |
| GCCA 12mer | GGC AGG CAG GCA (SEQ ID NO: 24) | EG3 | H |
| GCCA 12mer-B | GGC AGG CAG GCA (SEQ ID NO: 24) | EG3 | CP06062 |
| CAGG 24mer | CAG GCA GGC AGG CAG GCA GGC AGG (SEQ ID NO: 25) | EG3 | H |
| CAGG 24mer-B | CAG GCA GGC AGG CAG GCA GGC AGG (SEQ ID NO: 25) | EG3 | CP06062 |
| CAGG 24mer-R9F2 | CAG GCA GGC AGG CAG GCA GGC AGG (SEQ ID NO: 25) | EG3 | R9F2 |
| CAGG 24mer-rTat | CAG GCA GGC AGG CAG GCA GGC AGG (SEQ ID NO: 25) | EG3 | rTat |
| CAGG 9mer+ | C+AG GC+A GGC (SEQ ID NO: 26) | EG3 | H |
| CAGG 9mer+B | C+AG GC+A GGC (SEQ ID NO: 27) | EG3 | CP06062 |
| CAGG 9mer+ | C+AG GCA GGC (SEQ ID NO: 28) | EG3 | H |
| CAGG 9mer+ | CAG GC+A GGC (SEQ ID NO: 29) | EG3 | H |

*The linkage(s) between the oligonucleotide and the cell-penetrating peptide can included a variety of linkages, but preferred linkages are C, AhxB, G, and B.

Although the invention has been described with respect to certain embodiments and examples, it will be appreciated that various changes, modifications, and additions may be made without departing from the claimed invention.

REFERENCES

Abes, S., H. M. Moulton et al. (2006). "Vectorization of morpholino oligomers by the (R-Ahx-R)₄ peptide allows efficient splicing correction in the absence of endosomolytic agents." *J Control Release* 116(3): 304-13.

Arap, W. et al. (2004). "Human and mouse targeting peptides identified by phage display." U. S. Appn. Pubn. No. 20040170955.

Behlke, M. A. (2006). "Progress towards in vivo use of siRNAs." *Mol Ther* 13(4): 644-70.

Alter, J., F. Lou et al. (2006). "Systemic delivery of morpholino oligonucleotide restores dystrophin expression bodywide and improves dystrophic pathology." *Nat Med* 12(2): 175-7.

Chen, C. P., L. R. Zhang et al. (2003). "A concise method for the preparation of peptide and arginine-rich peptide-conjugated antisense oligonucleotide." *Bioconjug Chem* 14(3): 532-8.

Gebski, B. L., C. J. Mann et al. (2003). "Morpholino antisense oligonucleotide induced dystrophin exon 23 skipping in mdx mouse muscle." *Hum Mol Genet* 12(15): 1801-11.

Jearawiriyapaisarn, Moulton et al. (2008). "Sustained Dystrophin Expression Induced by Peptide-conjugated Morpholino Oligomers in the Muscles of mdx Mice." *Mol Therapy*, Jun. 10, 2008 (advance online publication).

Kang, S. H., M. J. Cho et al. (1998). "Up-regulation of luciferase gene expression with antisense oligonucleotides: implications and applications in functional assay development." *Biochemistry* 37(18): 6235-9.

Kolonin, M. G., J. Sun et al. (2006). "Synchronous selection of homing peptides for multiple tissues by in vivo phage display." *FASEB J* 20(7): 979-81.

Meade, B. R. and S. F. Dowdy (2007). "Exogenous siRNA delivery using peptide transduction domains/cell penetrating peptides." *Adv Drug Deliv Rev* 59(2-3): 134-40.

Richard, J. P., K. Melikov et al. (2003). "Cell-penetrating peptides. A reevaluation of the mechanism of cellular uptake." *J Biol Chem* 278(1): 585-90.

Rothbard, J. B., E. Kreider et al. (2002). "Arginine-rich molecular transporters for drug delivery: role of backbone spacing in cellular uptake." *J Med Chem* 45(17): 3612-8.

Samoylova, T. I. and B. F. Smith (1999). "Elucidation of muscle-binding peptides by phage display screening." *Muscle Nerve* 22(4): 460-6.

Sazani, P., F. Gemignani et al. (2002). "Systemically delivered antisense oligomers upregulate gene expression in mouse tissues." *Nat Biotechnol* 20(12): 1228-33.

Sontheimer, E. J. (2005). "Assembly and function of RNA silencing complexes." *Nat Rev Mol Cell Biol* 6(2): 127-38.

Vodyanoy, V. et al. (2003). "Ligand sensor devices and uses thereof." U. S. Appn. Pubn. No. 20030640466.

Wu, R. P., D. S. Youngblood et al. (2007). "Cell-penetrating peptides as transporters for morpholino oligomers: effects of amino acid composition on intracellular delivery and cytotoxicity." *Nucleic Acids Res.* 35(15):5182-91. (Epub 2007 Aug. 1.)

Youngblood, D. S., S. A. Hatlevig et al. (2007). "Stability of cell-penetrating peptide-morpholino oligomer conjugates in human serum and in cells." *Bioconjug Chem* 18(1): 50-60.

Dansithong, W., S. Paul, et al. (2005). "MBNL1 is the primary determinant of focus formation and aberrant insulin receptor splicing in DM1." *J Biol Chem* 280(7): 5773-80.

Mankodi, A., E. Logigian, et al. (2000). "Myotonic dystrophy in transgenic mice expressing an expanded CUG repeat." *Science* 289 (5485): 1769-73.

Wheeler, T. M., K. Sobczak, et al. (2009). "Reversal of RNA dominance by displacement of protein sequestered on triplet repeat RNA." *Science* 325 (5938): 336-9.

Mulders, S. A., W. J. van den Broek, et al. (2009). "Triplet-repeat oligonucleotide-mediated reversal of RNA toxicity in myotonic dystrophy." *Proc Natl Acad Sci USA* 106(33): 13915-20.

Wheeler, T. M. and C. A. Thornton (2007). "Myotonic dystrophy: RNA-mediated muscle disease." *Curr Opin Neurol* 20(5): 572-6.

Sequence Listing Table

| Sample Name | Sequence | SEQ ID NO: |
|---|---|---|
| CAG 9mer | CAG CAG CAG | 1 |
| CAG 12mer | CAG CAG CAG CAG | 2 |
| CAG 15mer | CAG CAG CAG CAG CAG | 3 |
| CAG 18mer | CAG CAG CAG CAG CAG CAG | 4 |
| AGC 9mer | AGC AGC AGC | 5 |
| AGC 12mer | AGC AGC AGC AGC | 6 |
| AGC 15mer | AGC AGC AGC AGC AGC | 7 |
| AGC 18mer | AGC AGC AGC AGC AGC AGC | 8 |
| GCA 9mer | GCA GCA GCA | 9 |
| GCA 12mer | GCA GCA GCA GCA | 10 |
| GCA 15mer | GCA GCA GCA GCA GCA | 11 |
| GCA 18mer | GCA GCA GCA GCA GCA GCA | 12 |
| AGC 25mer | AGC AGC AGC AGC AGC AGC AGC AGC A | 13 |
| CAG 25mer | CAG CAG CAG CAG CAG CAG CAG CAG C | 14 |
| CAG 9mer+ | C+AG C+AG C+AG | 15 |
| CAG 9mer+ | C+AG CAG CAG | 16 |
| CAG 9mer+ | CAG CAG C+AG | 17 |
| CAG 9mer+ | CAG C+AG CAG | 18 |
| CAGG 9mer | CAG GCA GGC | 19 |
| CAGG 12mer | CAG GCA GGC AGG | 20 |
| AGGC 9mer | AGG CAG GCA | 21 |
| AGGC 12mer | AGG CAG GCA GGC | 22 |
| GGCA 9mer | GGC AGG CAG | 23 |
| GGCA 12mer | GGC AGG CAG GCA | 24 |
| CAGG 24mer | CAG GCA GGC AGG CAG GCA GGC AGG | 25 |
| CAGG 9mer+ | C+AG GC+A GGC | 26 |
| CAGG 9mer+B | C+AG GC+A GGC | 27 |
| CAGG 9mer+ | C+AG GCA GGC | 28 |
| CAGG 9mer+ | CAG GC+A GGC | 29 |
| rTAT | RRRQRRKKR | 30 |
| Tat | RKKRRQRRR | 31 |
| $R_9F_2$ | RRRRRRRRRFF | 32 |
| $R_5F_2R_4$ | RRRRRFFRRRR | 33 |
| $R_4$ | RRRR | 34 |
| $R_5$ | RRRRR | 35 |
| $R_6$ | RRRRRR | 36 |
| $R_7$ | RRRRRRR | 37 |

Sequence Listing Table

| Sample Name | Sequence | SEQ ID NO: |
|---|---|---|
| $R_8$ | RRRRRRRR | 38 |
| $R_9$ | RRRRRRRRR | 39 |
| $(RAhxR)_4$; (P007) | RAhxRRAhxRRAhxRRAhxR | 40 |
| $(RAhxR)_5$; (CP04057) | RAhxRRAhxRRAhxRRAhxRRAhxR | 41 |
| $(RAhxRRBR)_2$; (CP06062) | RAhxRRBRRAhxRRBR | 42 |
| $(RAR)_4F_2$ | RARRARRARRARFFC | 43 |
| $(RGR)_4F_2$ | RGRRGRRGRRGRFFC | 44 |
| SMP1 | ASSLNIA | 45 |
| SMP2 | SLGSFP | 46 |
| SMP3 | SGASAV | 47 |
| SMP4 | GRSGAR | 48 |
| SMP5 | TARGEHKEEELI | 49 |
| CMP1 | WLSEAGPVVTVRALRGTGSW | 50 |
| CMP2 | VTVRALRGTSW | 51 |
| CMP3 | VVTVRALRGTGSW | 52 |
| CMP4 | CRPPR | 53 |
| CMP5 | SKTFNTHPQSTP | 54 |
|  | (RXRR(X/B)R)$_2$XB | 55 |
|  | CRVASVLPC | 56 |

*In SEQ ID NOS: 15-18 and 26-29, "+" refers to a cationic linkage, such as 1-piperazinyl.

---

It is claimed:

1. An antisense compound, comprising an uncharged antisense oligomer of 8-30 bases comprising a sequence of at least 8 contiguous bases that is complementary to: (i) the polyCUG repeats in the 3'-UTR region of dystrophia myotonica protein kinase (DMPK) mRNA in Myotonic dystrophy type 1 (DM1) or (ii) the polyCCUG repeats in the first intron of zinc finger protein 9 (ZNF9) mRNA in Myotonic dystrophy type 2 (DM2), and a cell-penetrating peptide (CPP) conjugated to the oligomer, wherein the CPP is of a formula selected from the group consisting of:

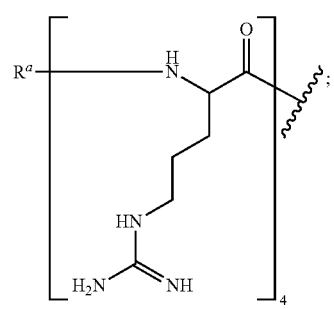

(SEQ ID NO: 34)

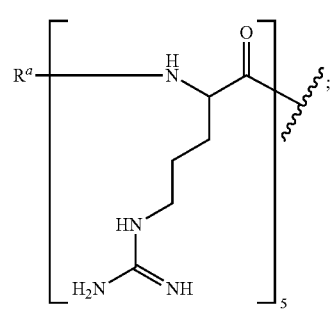

(SEQ ID NO: 35)

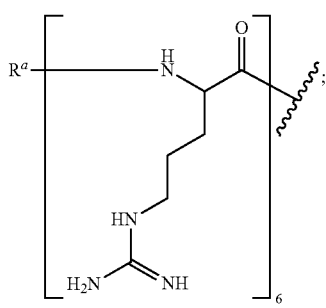

(SEQ ID NO: 36)

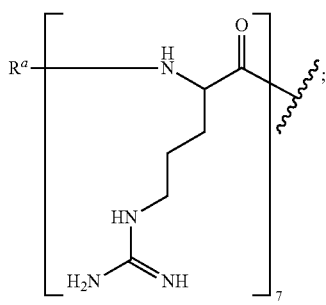

(SEQ ID NO: 37)

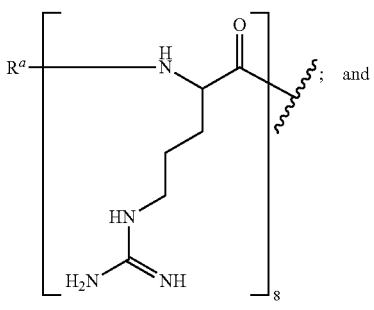

(SEQ ID NO: 38); and (SEQ ID NO: 39)

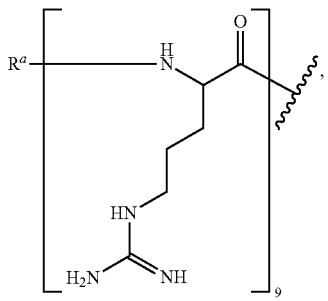

wherein independently for each instance $R^a$ is H or acetyl.

2. The antisense compound of claim 1, wherein the CPP is conjugated to the antisense oligomer with a linker selected from glycine (G), cysteine (C), 6-aminohexanoic acid (Ahx), β-alanine (B), and AhxB.

3. The antisense compound of claim 2, wherein the linker is G.

4. The antisense compound of claim 2, wherein the CPP and linker together are of a formula selected from the group consisting of:

(SEQ ID NO: 57)

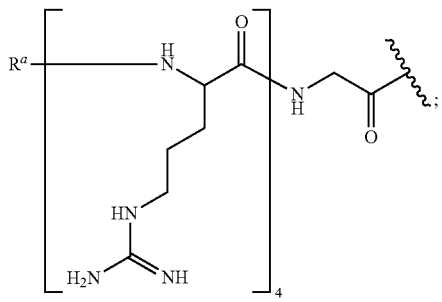

(SEQ ID NO: 58)

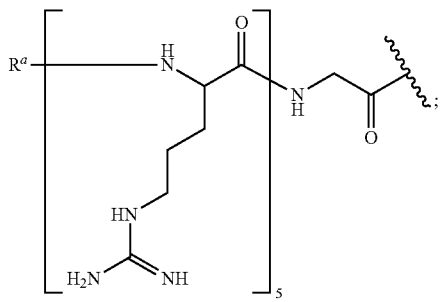

(SEQ ID NO: 59)

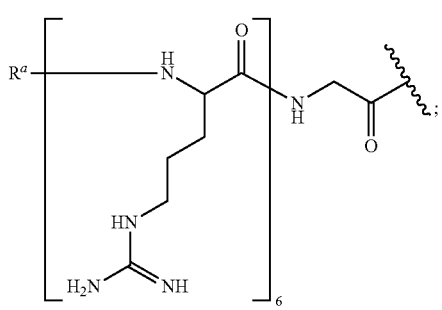

(SEQ ID NO: 60)

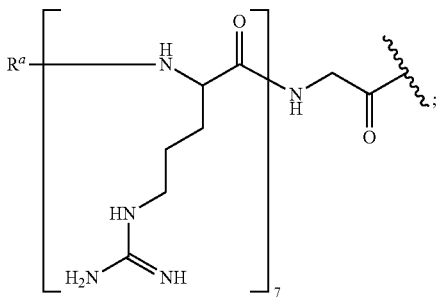

(SEQ ID NO: 61)

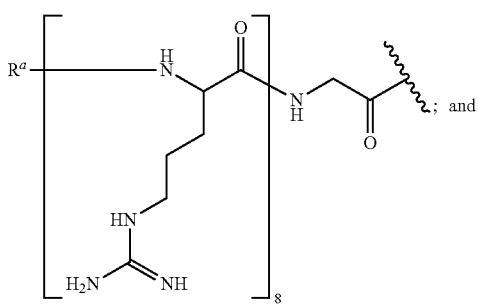

(SEQ ID NO: 62)

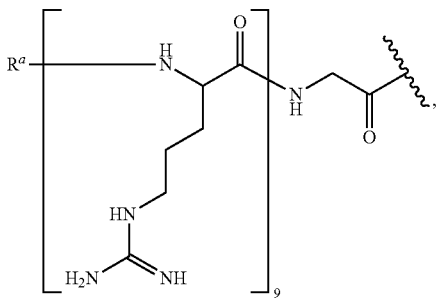

wherein independently for each instance $R^a$ is H or acetyl.

5. The antisense compound of claim 1, wherein the antisense oligomer is a phosphorodiamidate morpholino oligomer (PMO) having a sequence complementary to the polyCUG repeats in the 3'-UTR region of dystrophia myotonica protein kinase (DMPK) mRNA in DM1.

6. The antisense compound of claim 5, wherein the sequence is selected from SEQ ID NOs: 1-14.

7. The antisense compound of claim 1, wherein the antisense oligomer is a phosphorodiamidate morpholino oligomer (PMO) having a sequence complementary to the polyCCUG repeats in the first intron of zinc finger protein 9 (ZNF9) mRNA in DM2.

8. The antisense compound of claim 7, wherein the sequence is selected from SEQ ID NOs: 19-25.

9. An antisense compound, comprising:
an antisense oligomer of 8-30 morpholino subunits linked together by phosphorodiamidate linkages, wherein:
each morpholino subunit is of a formula:

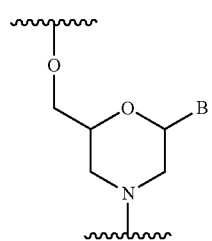

wherein each B is a base pairing moiety independently selected from adenine, cytosine, guanine, uracil, thymine or hypoxanthine, wherein each B taken together comprises a sequence of at least 8 contiguous bases that is complementary to: (i) the polyCUG repeats in the 3'UTR region of dystrophia myotonica protein kinase (DMPK) mRNA in Myotonic dystrophy type 1 (DM1) or (ii) the polyCCUG repeats in the first intron of zinc finger protein 9 (ZNF9) mRNA in Myotonic dystrophy type 2 (DM2); and each phosphorodiamidate linkage is of a formula:

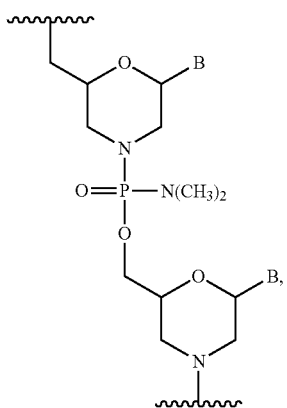

and a cell-penetrating peptide (CPP) conjugated to the morpholino oligomer, wherein:

the CPP is of a formula selected from the group consisting of:

(SEQ ID NO: 34)

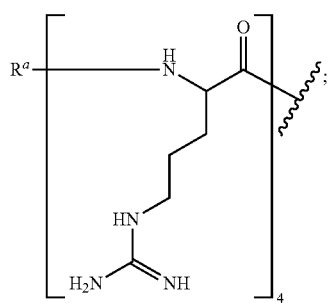

(SEQ ID NO: 35)

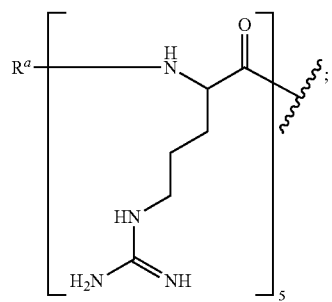

(SEQ ID NO: 36)

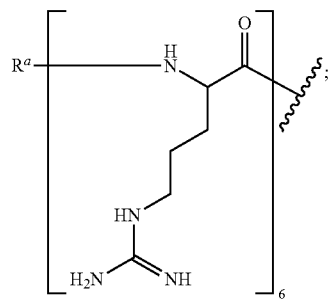

(SEQ ID NO: 37)

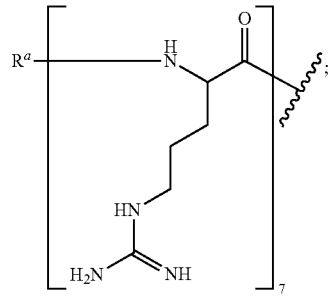

(SEQ ID NO: 38)

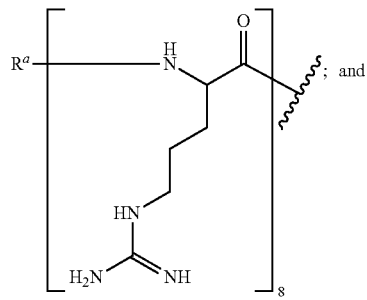

(SEQ ID NO: 39)

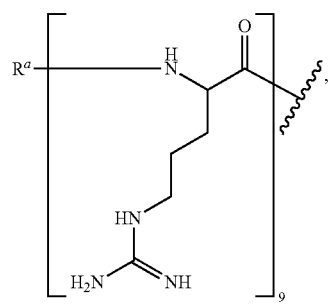

wherein independently for each instance $R^a$ is H or acetyl, and the CPP is conjugated to the morpholino oligomer by a linker selected from:

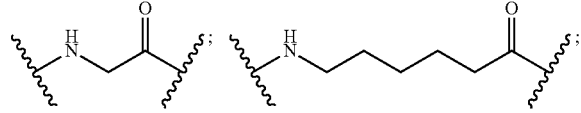

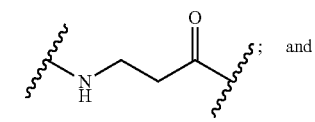 and

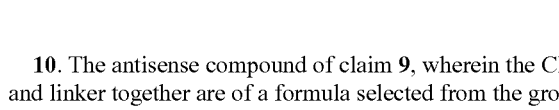

10. The antisense compound of claim 9, wherein the CPP and linker together are of a formula selected from the group consisting of:

(SEQ ID NO: 57)
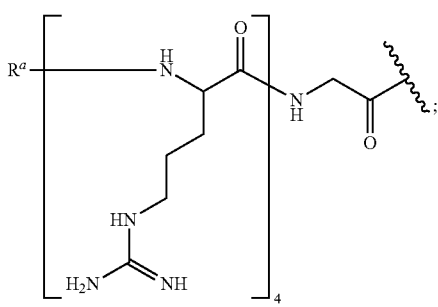

(SEQ ID NO: 58)
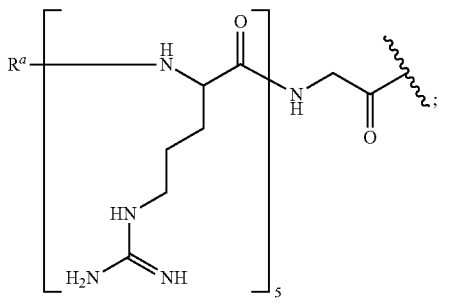

(SEQ ID NO: 59)
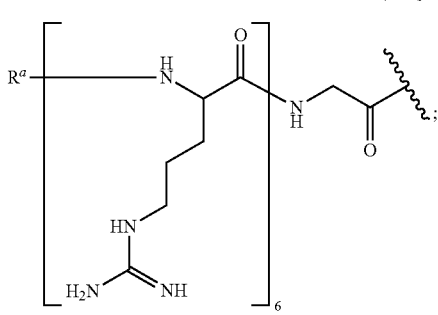

(SEQ ID NO: 60)
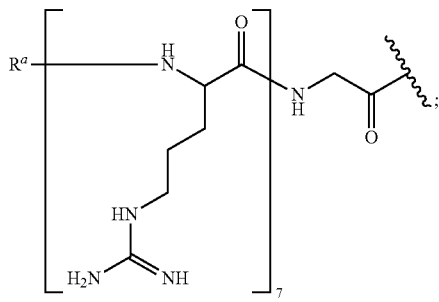

(SEQ ID NO: 61)
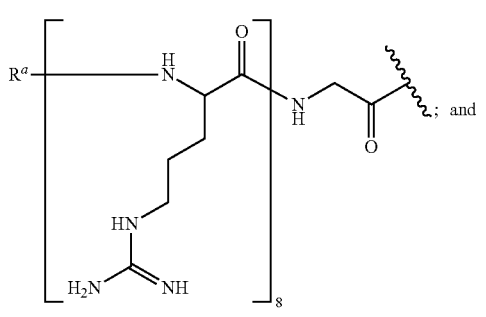

(SEQ ID NO: 62)
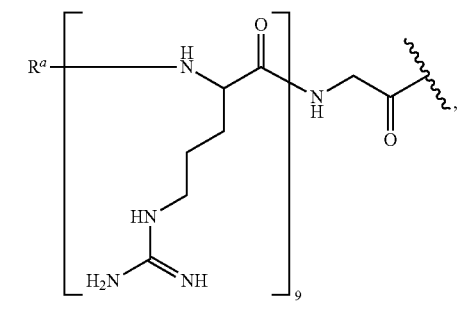

wherein independently for each instance $R^a$ is H or acetyl.

11. The antisense compound of claim 9, wherein the sequence is complementary to the polyCUG repeats in the 3'UTR region of dystrophia myotonica protein kinase (DMPK) mRNA in DM1.

12. The antisense compound of claim 11, wherein the sequence is selected from SEQ ID NOs: 1-14.

13. The antisense compound of claim 9, wherein the sequence is complementary to the polyCCUG repeats in the first intron of zinc finger protein 9 (ZNF9) mRNA in DM2.

14. The antisense compound of claim 13, wherein the sequence is selected from SEQ ID NOs: 19-25.

15. A method of treating myotonic dystrophy type 1 (DM1) or myotonic dystrophy type 2 (DM2) in a mammalian subject in need thereof, comprising administering to the subject an effective amount of an antisense compound, wherein the antisense compound comprises:

an antisense oligomer of 8-30 morpholino subunits linked together by phosophorodiamidate linkages, wherein:

each morpholino subunit is of a formula:

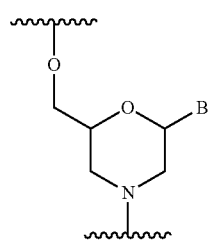

wherein each B is a base pairing moiety independently selected from adenine, cytosine, guanine, uracil, thymine or hypoxanthine, wherein each B taken together comprises a sequence of at least 8 contiguous bases that is complementary to: (i) the polyCUG repeats in the 3'UTR region of dystrophia myotonica protein kinase (DMPK) mRNA in Myotonic dystrophy type 1 (DM1) or (ii) the polyCCUG repeats in the first intron of zinc finger protein 9 (ZNF9) mRNA in Myotonic dystrophy type 2 (DM2); and each phosphorodiamidate linkage is of a formula:

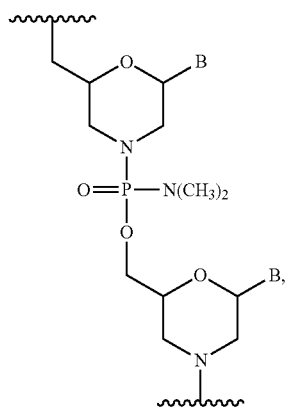

and a cell-penetrating peptide (CPP) conjugated to the morpholino oligomer, wherein:

the CPP is of a formula selected from the group consisting of:

(SEQ ID NO: 34)

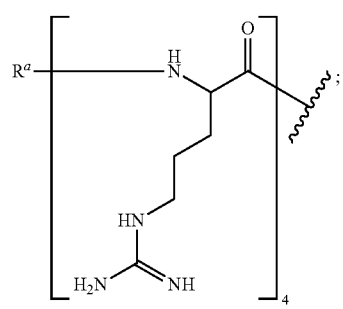

(SEQ ID NO: 35)

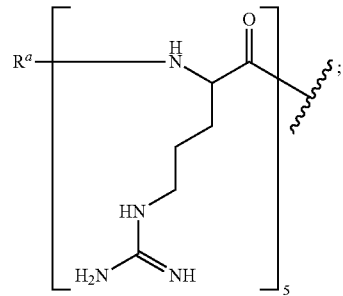

(SEQ ID NO: 36)

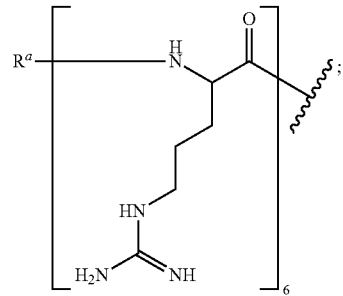

(SEQ ID NO: 37)

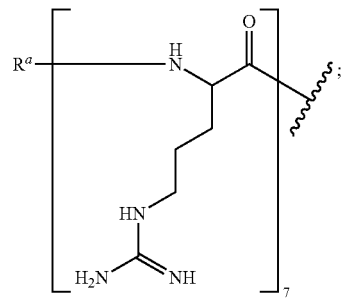

(SEQ ID NO: 38)

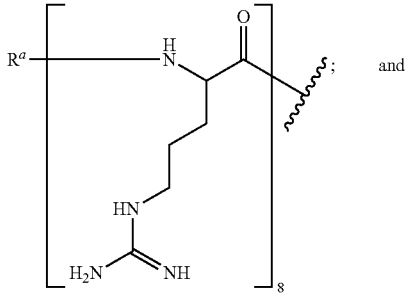

and (SEQ ID NO: 39)

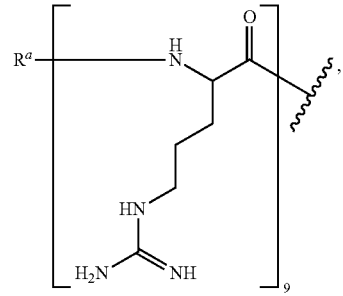

wherein independently for each instance $R^a$ is H or acetyl, and the CPP is conjugated to the morpholino oligomer by a linker selected from:

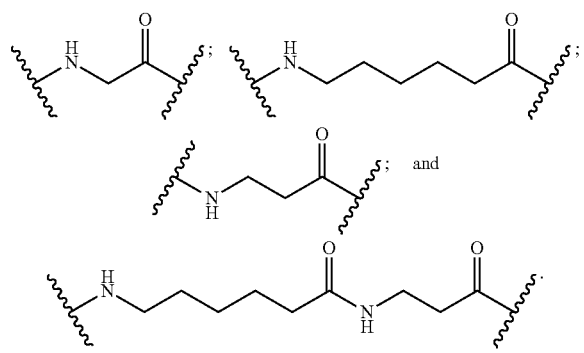

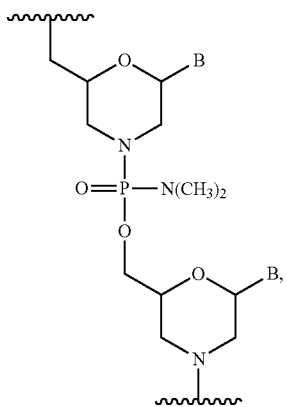

16. A pharmaceutical composition, comprising:
a pharmaceutically acceptable carrier and an antisense compound, wherein the antisense compound comprises:
an antisense oligomer of 8-30 morpholino subunits linked together by phosphorodiamidate linkages, wherein:
each morpholino subunit is of a formula:

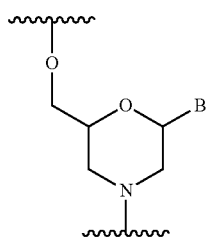

wherein each B is a base pairing moiety independently selected from adenine, cytosine, guanine, uracil, thymine or hypoxanthine, wherein each B taken together comprises a sequence of at least 8 contiguous bases that is complementary to: (i) the polyCUG repeats in the 3'UTR region of dystrophia myotonica protein kinase (DMPK) mRNA in Myotonic dystrophy type 1 (DM1) or (ii) the polyCCUG repeats in the first intron of zinc finger protein 9 (ZNF9) mRNA in Myotonic dystrophy type 2 (DM2); and
each phosphorodiamidate linkage is of a formula:

and
a cell-penetrating peptide (CPP) conjugated to the morpholino oligomer, wherein:
the CPP is of a formula selected from the group consisting of:

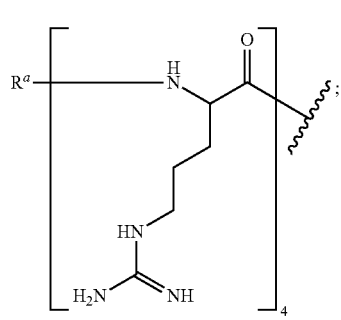
(SEQ ID NO: 34)

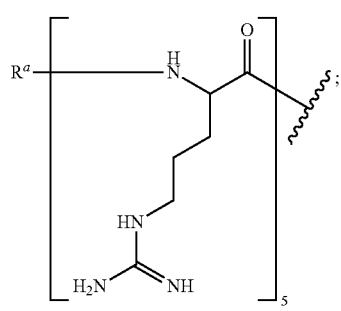
(SEQ ID NO: 35)

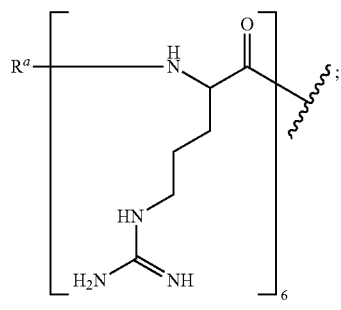
(SEQ ID NO: 36)

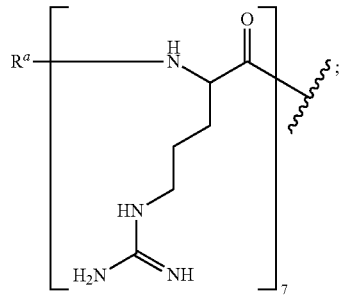
(SEQ ID NO: 37)

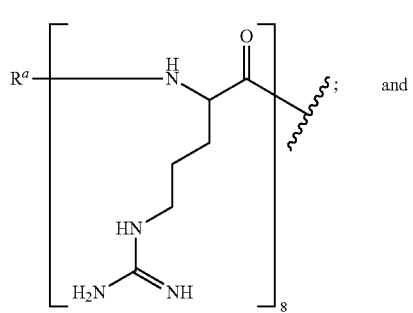
(SEQ ID NO: 38)
and

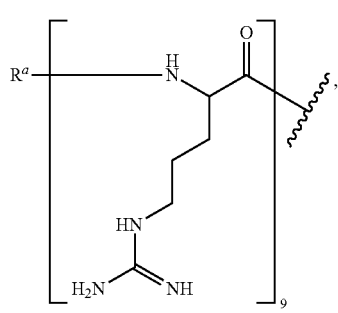
(SEQ ID NO: 39)
wherein independently for each instance $R^a$ is H or acetyl, and the CPP is conjugated to the morpholino oligomer by a linker selected from:
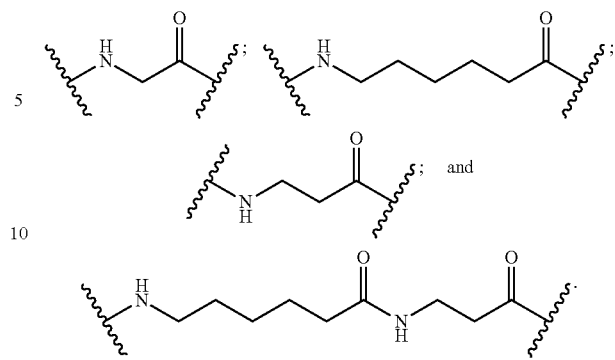
* * * * *